(12) United States Patent
Podhasky et al.

(10) Patent No.: US 12,343,720 B2
(45) Date of Patent: Jul. 1, 2025

(54) SYSTEM AND METHOD FOR POLYNUCLEOTIDE PURIFICATION

(71) Applicant: LIFE TECHNOLOGIES CORPORATION, Carlsbad, CA (US)

(72) Inventors: Joseph Podhasky, San Rafael, CA (US); Mark Reed, Menlo Park, CA (US); Nathan Kane, Guilford, CT (US)

(73) Assignee: Life Technologies Corporation, Carlsbad, CA (US)

( * ) Notice: Subject to any disclaimer, the term of this patent is extended or adjusted under 35 U.S.C. 154(b) by 63 days.

(21) Appl. No.: 17/526,979

(22) Filed: Nov. 15, 2021

(65) Prior Publication Data

US 2022/0176369 A1   Jun. 9, 2022

Related U.S. Application Data

(60) Provisional application No. 63/113,972, filed on Nov. 15, 2020.

(51) Int. Cl.
*B01L 3/00* (2006.01)
*B01L 3/02* (2006.01)

(52) U.S. Cl.
CPC ........... *B01L 3/0237* (2013.01); *B01L 3/0224* (2013.01); *B01L 3/50855* (2013.01); *B01L 2200/04* (2013.01); *B01L 2200/0605* (2013.01); *B01L 2200/16* (2013.01); *B01L 2300/0663* (2013.01); *B01L 2300/0829* (2013.01)

(58) Field of Classification Search
CPC ...... G01N 27/72; G01N 33/15; B06B 1/0207; B06B 1/0662; B06B 1/0651; B06B 2201/77
See application file for complete search history.

(56) References Cited

U.S. PATENT DOCUMENTS 10,401,373 B1    9/2019  Holmes et al.
2021/0230579 A1* 7/2021  Park ................... B01L 3/50853

FOREIGN PATENT DOCUMENTS

| CN | 206583802 U | | 10/2017 |
|---|---|---|---|
| CN | 110511865 A | | 11/2019 |
| CN | 110923124 A | | 3/2020 |
| KR | 20200012291 A | * | 2/2020 |
| WO | WO-2020001493 A1 | | 1/2020 |
| WO | WO-2020022742 A1 | | 1/2020 |

OTHER PUBLICATIONS

PCT/US2021/059410, International Search Report and Written Opinion, Mar. 7, 2022, 13 pages.

* cited by examiner

*Primary Examiner* — Jill A Warden
*Assistant Examiner* — Michael Stanley Gzybowski

(57) ABSTRACT

A system includes a pipetting system including a 3-axis gantry; a sled mechanism to select a magnetic comb from a set of magnetic combs; a fluorometer; and a set of receptacles to receive welled plates. A method for purifying nucleic acids includes applying a sample to a well of a multi-well plate, selecting a magnetic comb from a set of magnetic combs disposed on a gantry system, collecting magnetic beads using the magnetic comb, collecting nucleic acid using the magnetic beads, and eluting the nucleic acid from the beads.

12 Claims, 25 Drawing Sheets

SYSTEM AND METHOD FOR POLYNUCLEOTIDE PURIFICATION

CROSS-REFERENCE TO RELATED APPLICATION(S)

This application claims benefit of U.S. Provisional Application No. 63/113,972, filed Nov. 15, 2020, which is incorporated herein by reference in its entirety.

FIELD OF THE DISCLOSURE

This disclosure, in general, relates to systems and methods for purifying polynucleotides from samples.

BACKGROUND

Increasingly, genetic sequencing is being used as a tool in both research and clinical settings. For example, research into the origins of disease, differentiations of species, characteristics of microbiomes, and the study of both bacterial and viral pathogens is being performed using genetic sequencing. In another example, genetic testing is increasingly being used to detect cancers, trace viral infections, prescribed diets, and modify prescription formularies.

With the increased interest in use of genetic sequencing, demand is rising for automated solutions to extract nucleic acid from many sources using different techniques. For example, techniques for extraction of Formalin Fixed Paraffin Embedded (FFPE) samples, biopsies, or blood sources, among others. In particular, cell free DNA recovered from blood or plasma is increasingly becoming of interest. Moreover, extracting nucleic acids, such as DNA or RNA, from a plurality of samples simultaneously is of interest, particularly in clinical settings. As such, a systems and methods for multiplex extraction of nucleic acids would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an example embodiment, an instrument includes a pipetting system having three axis movement, a sled mechanism configured to select comb magnets from a pair of comb magnets, a deck including supports for securing protective comb covers, and receptacles to receive a first type of welled plates and receptacles to receive a second type of welled plates. The instrument can further include a fluorometer and an associated receptacle to store reagents. In addition, the deck of the instrument can include a receptacle to receive a transfer plate and a receptacle to receive an archive plate. The deck may also include receptacles to receive trays of pipette tips.

The instrument can extract nucleic acids, such as deoxyribonucleic acid (DNA) or ribonucleic acid (RNA), by selecting a magnetic comb using a slide mechanism. The instrument can select a magnetic comb based on a type of samples to be extracted. Using the pipette system, samples and reagents can be mixed. Reagents can include magnetic particles. Utilizing the selected magnetic comb, nucleic acids coupled to magnetic particles can be separated from other components within the sample. A concentration of the extracted nucleic acids can be determined utilizing the quantification fluorometer. A portion of the extracted samples can be stored on the transfer plate to be transferred to a sequencing instrument. Remaining extracted solution can be stored on an archive plate.

Figure 1:
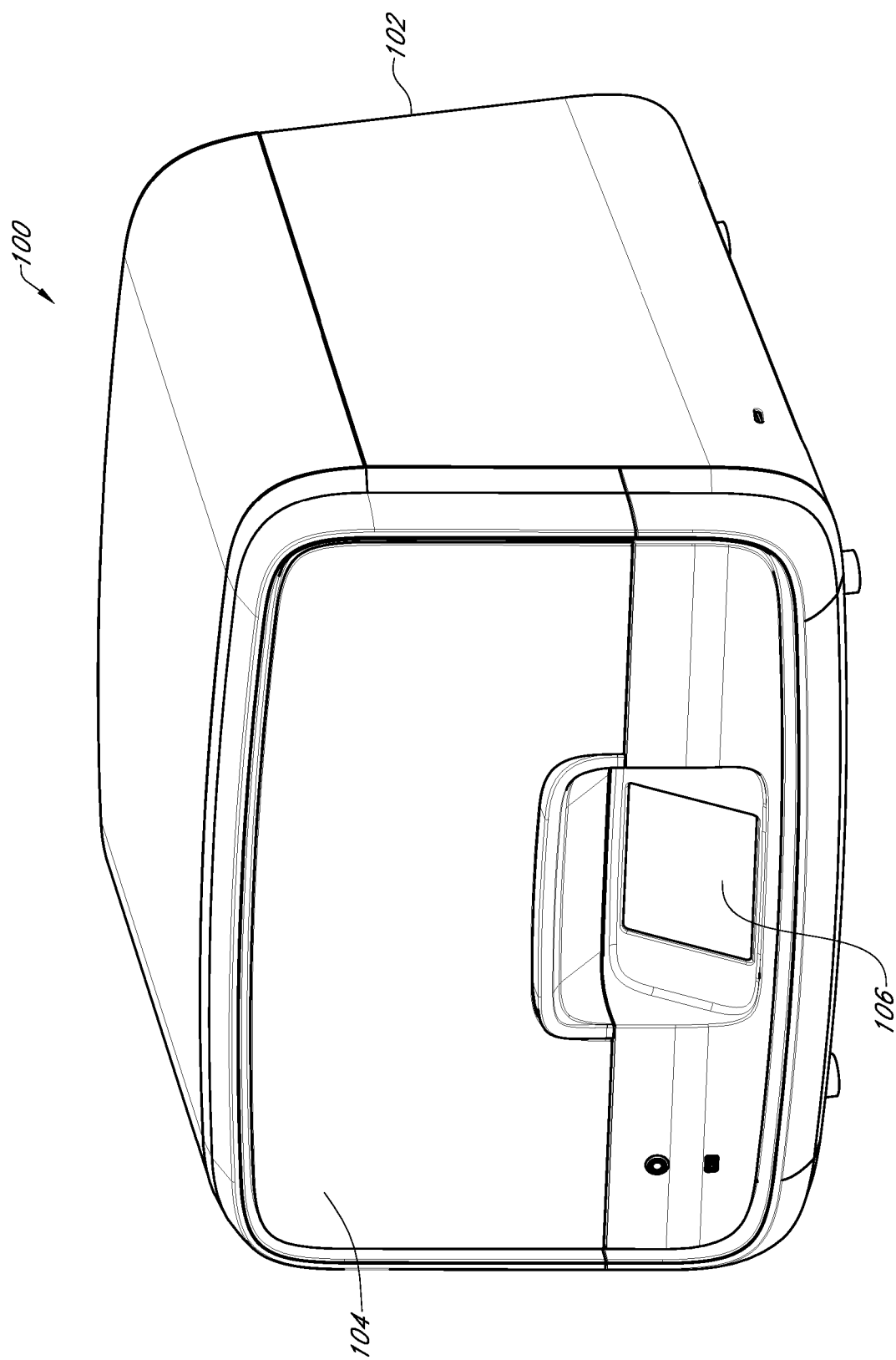
FIG. 1 includes an illustration of an exemplary purification instrument.

FIG. 1 includes an illustration of an example instrument 100 for extracting nucleic acids from samples. The instrument 100 includes an outer shell 102, a door 104 to access the inner workings of the instrument 104, and a user interface 106, such as a touchscreen interface. Alternatively, the user interface can include monitors physical keyboards or pointer devices.

Figure 2:
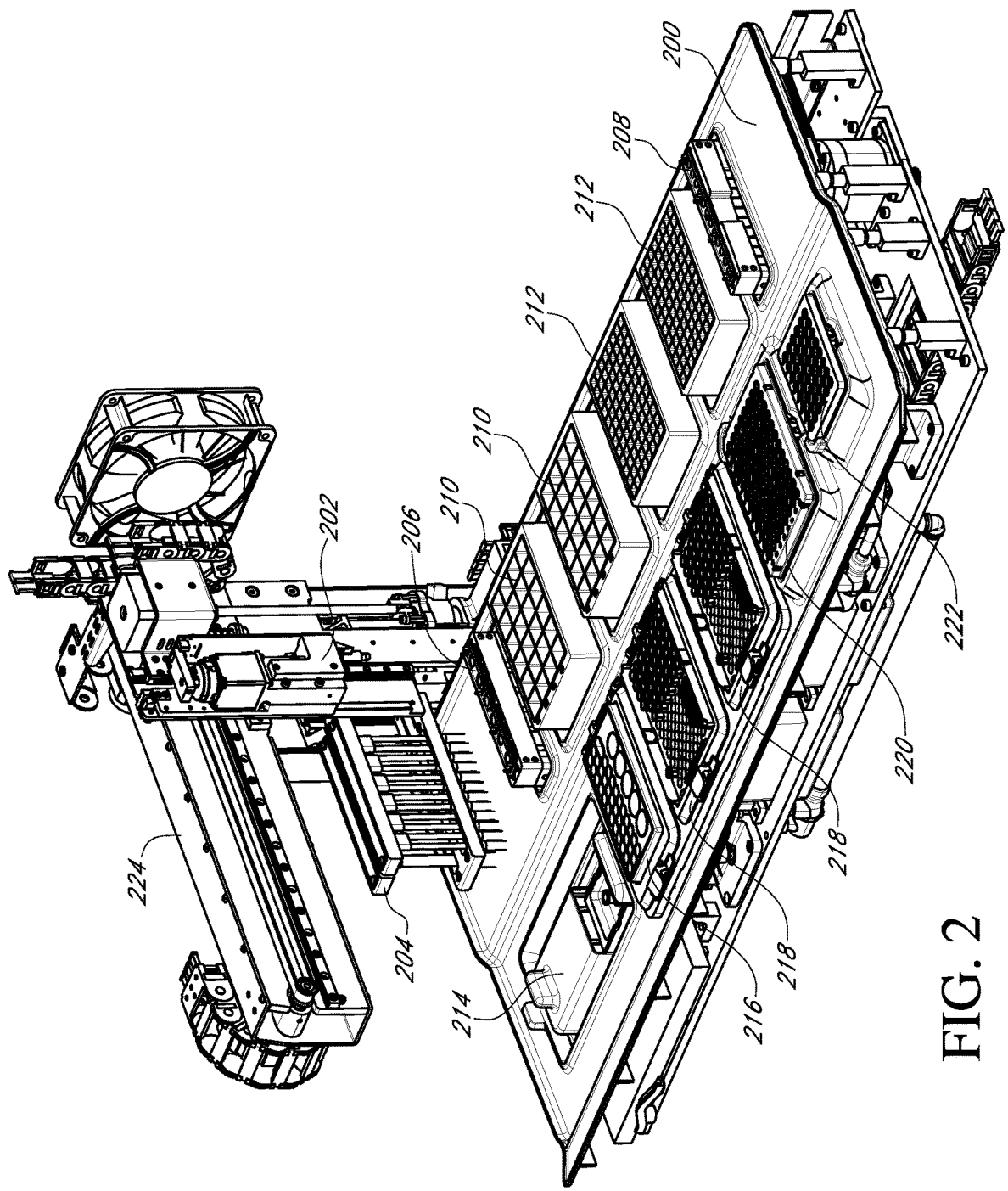
FIG. 2 includes an illustration of an example deck associated with the purification instrument.

FIG. 2 includes an illustration of example inner workings of the purification instrument 100. For example, the system can include a deck 200 and a pipetting system 202, including a three-axis gantry 224. In addition, the system can include a sled mechanism 204 for selecting a magnetic comb from a set of magnetic combs. A deck 200 can include receptacles 206 and 208 to secure magnetic comb covers. The deck 200 can also include receptacles for a set of first welled plates 210 and second set of welled plates 212. For example, the first welled plates 210 can be 24-well plates. In another example, the second welled plates 212 can be 96-well plates. The deck 200 can also include receptacles for arrays 218 of pipette tips.

Optionally, the system includes a fluorometer 214. The deck 200 can include a receptacle for a reagent plate 216 for storing reagents, including reagents for use with the fluorometer 214 and optionally including reagents for eluting nucleic acids.

Extracted nucleic acid samples can be stored on a transfer plate 220. Remaining extracted solutions can be archived on the archive plate 222.

Figure 3:
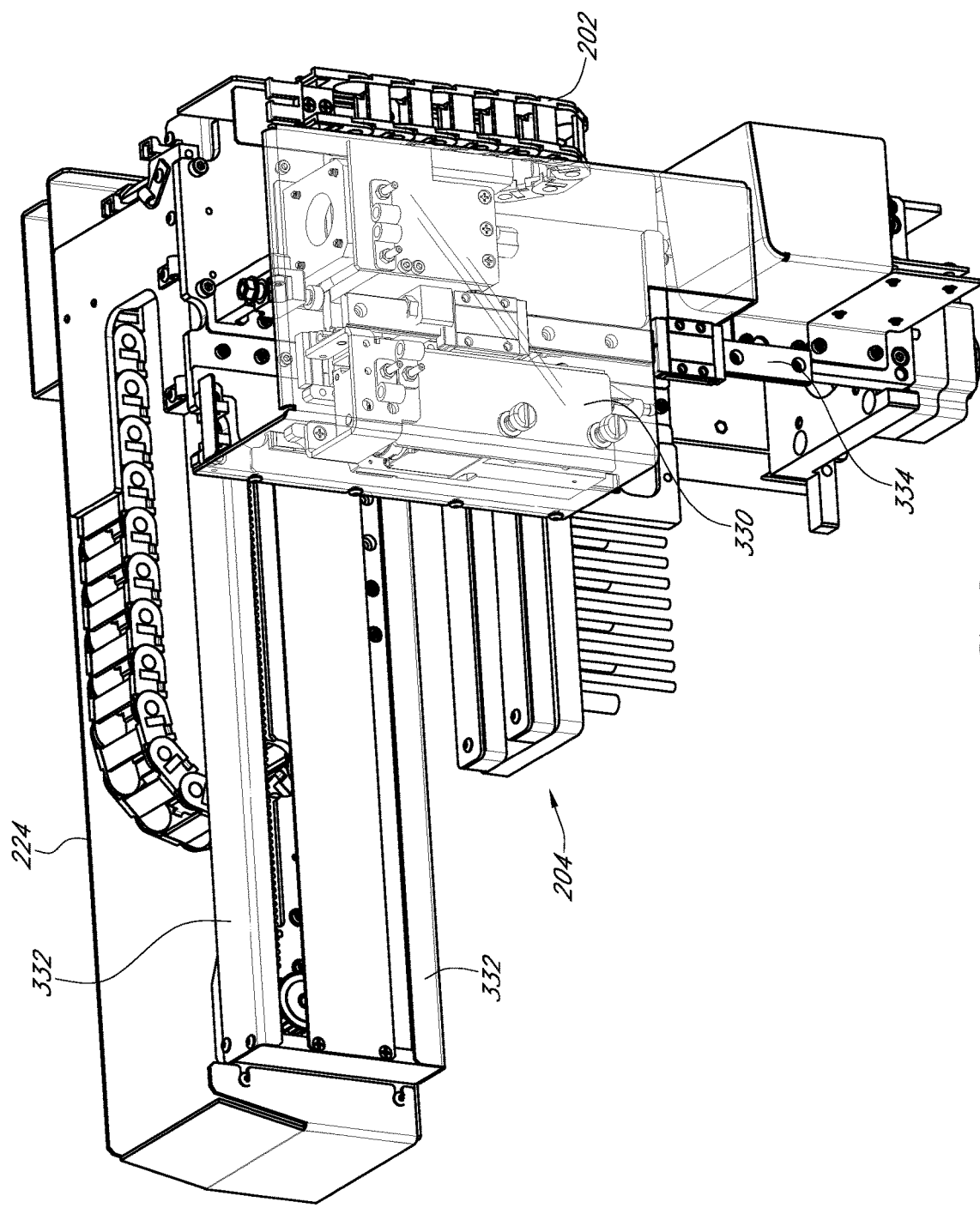
FIG. 3 includes an illustration of an example pipetting gantry of the purification instrument.

FIG. 3 includes an illustration of three-axis pipetting system 202. A gantry 224 can include guides 332 for moving the pipette pump 330 along a first horizontal dimension. The entire gantry 224 and pipette system 202 can move horizontally along the second horizontal axis. The system can further include a rail 334 along which the pipette pump 330 is moved vertically.

Figure 4:
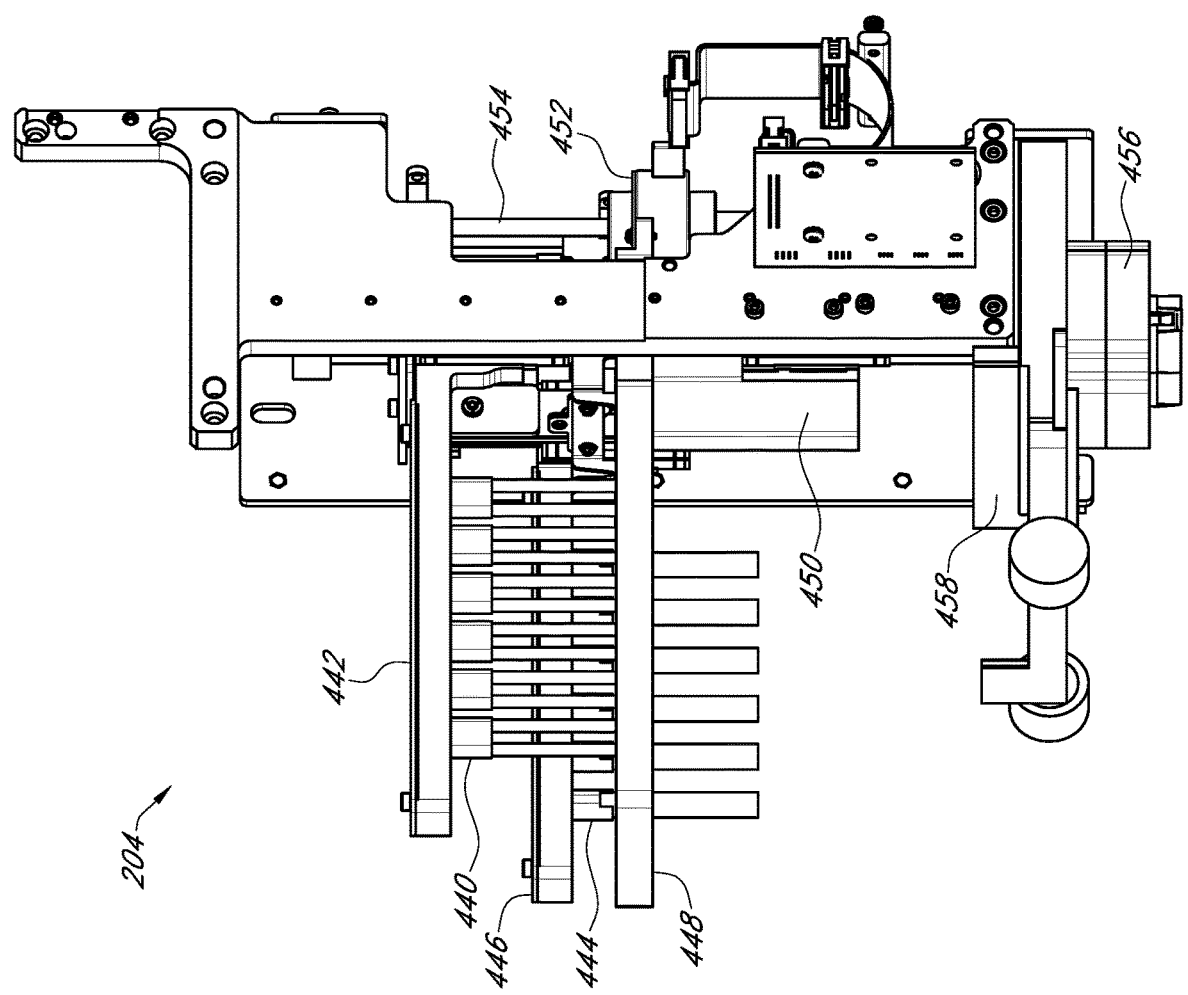
FIG. 4, FIG. 5, FIG. 6, FIG. 7, FIG. 8, and FIG. 9 include illustrations of an example sled system for selectively utilizing magnetic combs.

A sled mechanism 204 includes a set of magnetic combs attached to arms. For example, the sled mechanism 204 can include a magnetic comb 440 attached to arm 442 and a magnetic comb 444 attached to the arm 446, as illustrated in FIG. 4. The arms 442 and 446 are positioned above a platform 448 attached to a sled 450.

Figure 5:
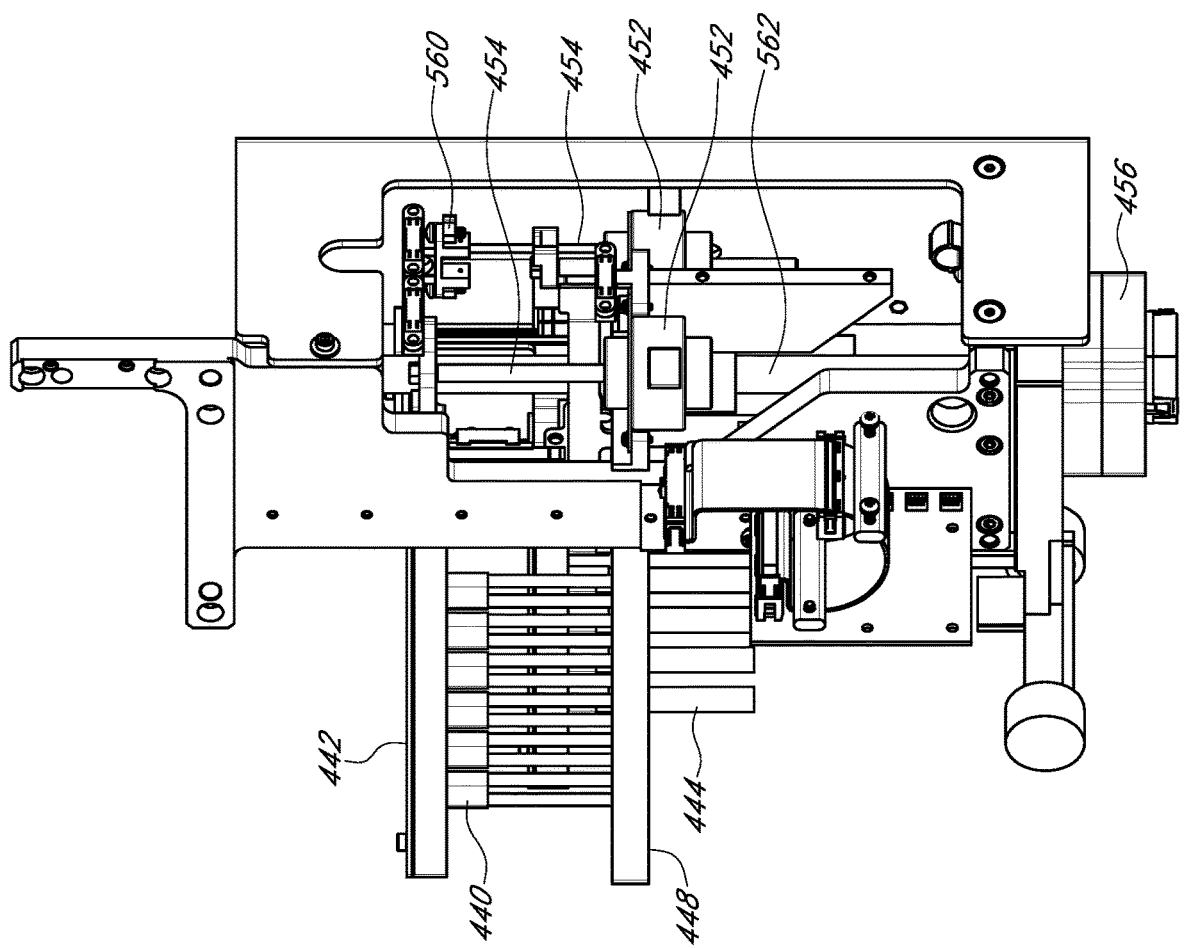

A motor 456 can move the sled 450 in vertical directions above the base 458 along a rod 562. For example, as illustrated in FIG. 5, the motor 456 can rotate rod 562 to move the sled 450 up and down along the rod 562. Alternatively, a piston system can be used. Drives 452 attached to the sled 450 can use rods 454 to drive the arms 442 or 446 up and down relative to the platform 448.

Figure 6:
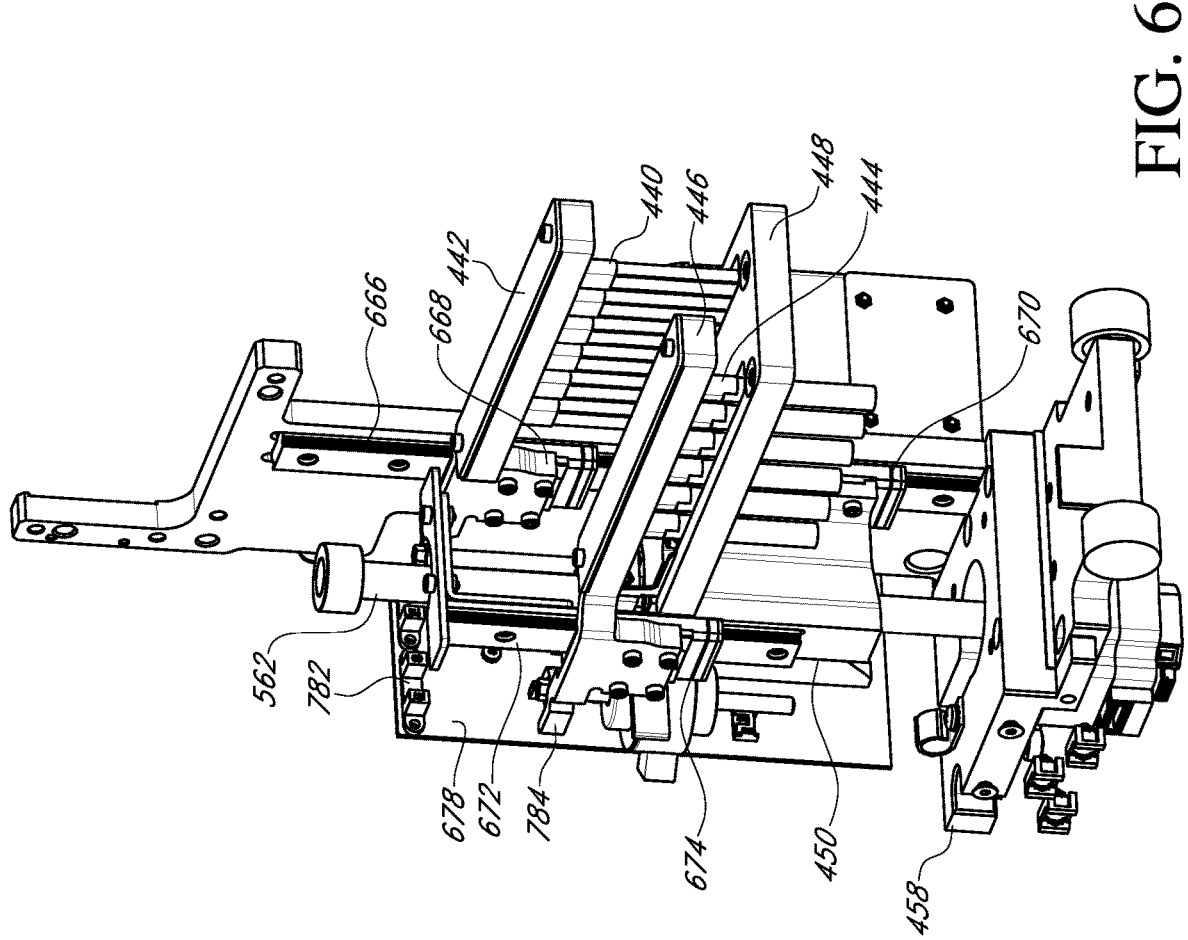

The sled mechanism 204 can select one magnetic comb of the set of magnetic combs by moving one of the combs and associated arm away from the platform 448 while moving the other comb and arm into proximity with the platform. The selected magnetic comb extends through the platform 448. The arms 442 or 446 can be independently moved by the separate motors 452 and associated rods 454. For example, the arm 446 attached to the magnetic comb 444 can be moved up and down utilizing one of the motors 452 along rail 672 attached to a slide 674 coupled to the arm 446, as illustrated in FIG. 6. The rail 672 can be coupled to the sled 450. In another example, the arm 442 coupled with comb 440 can move up and down relative to the platform 448 using one of the motors 452. The arm 442 is attached to a slide 668 connected with the rail 666 secured to a frame of the system. The sled 450 can also be attached to a slide 676 that is coupled to the rail 666.

The circuit board 678 coupled with the slide 450 can also secure sensors 782. The circuit board 678 moves with the slide 450 up-and-down in response to the drive 456. As such, the position of sensors 782 is fixed relative to the slide 450, as illustrated in FIG. 6.

In an example, the set of combs can have a different number of magnetic rods. The combs can include between 4 and 20 magnetic rods. In an example, the second comb has twice the number of magnetic rods as the first comb. For example, a first comb of the set of combs can include 6 magnetic rods. In another example, a comb of the set of combs can include 12 magnetic rods.

Figure 7:
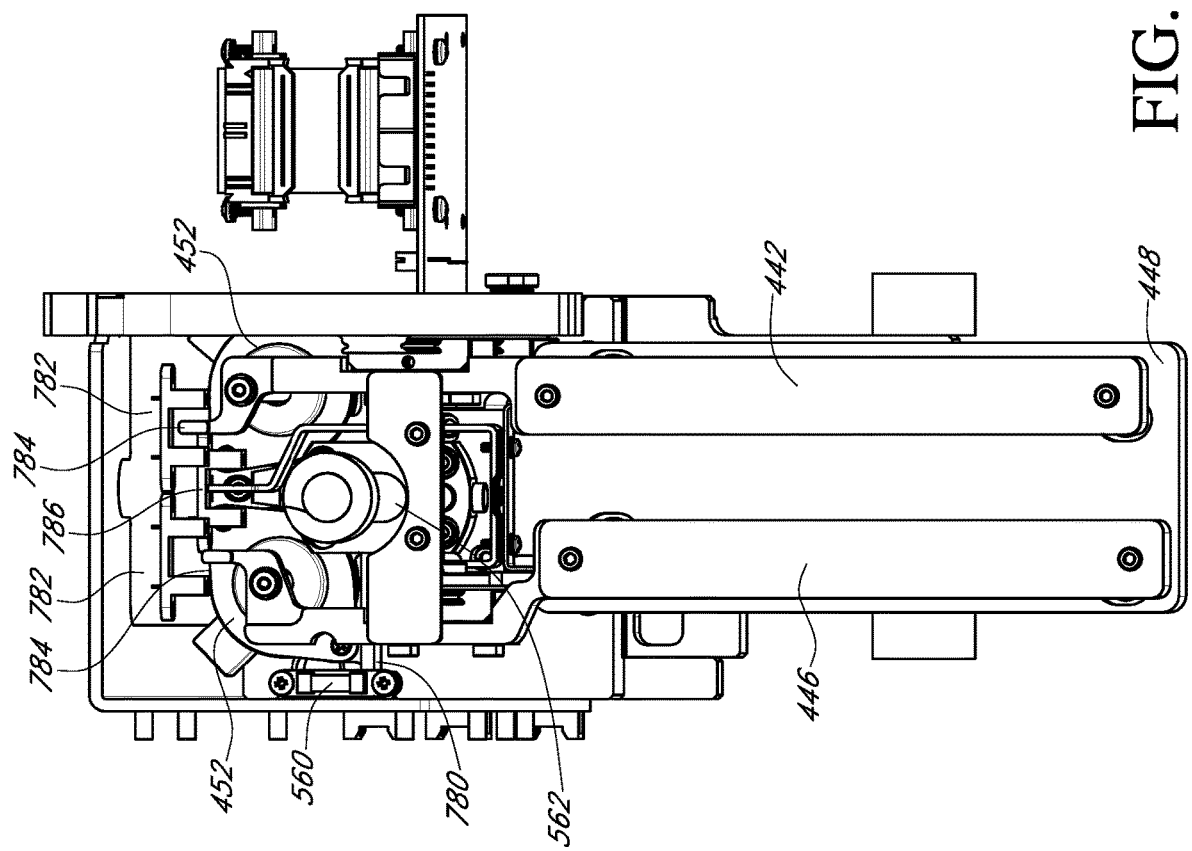

The arms 442 or 446 move up and down relative to the sled 450. In an example, the arms 442 or 446 include extensions 784 that can be detected by position sensors 782, as illustrated in FIG. 7. In particular, when the arms 442 or 446 are at their maximum height relative of the sled 450, the extension 784 is detected by sensors 782, indicating that the arm is at its maximum height relative to the sled 450. The sled 450 can also include an extension 780 that interacts with a sensor 560 that indicates when the sled 450 is at its maximum height.

Figure 8:
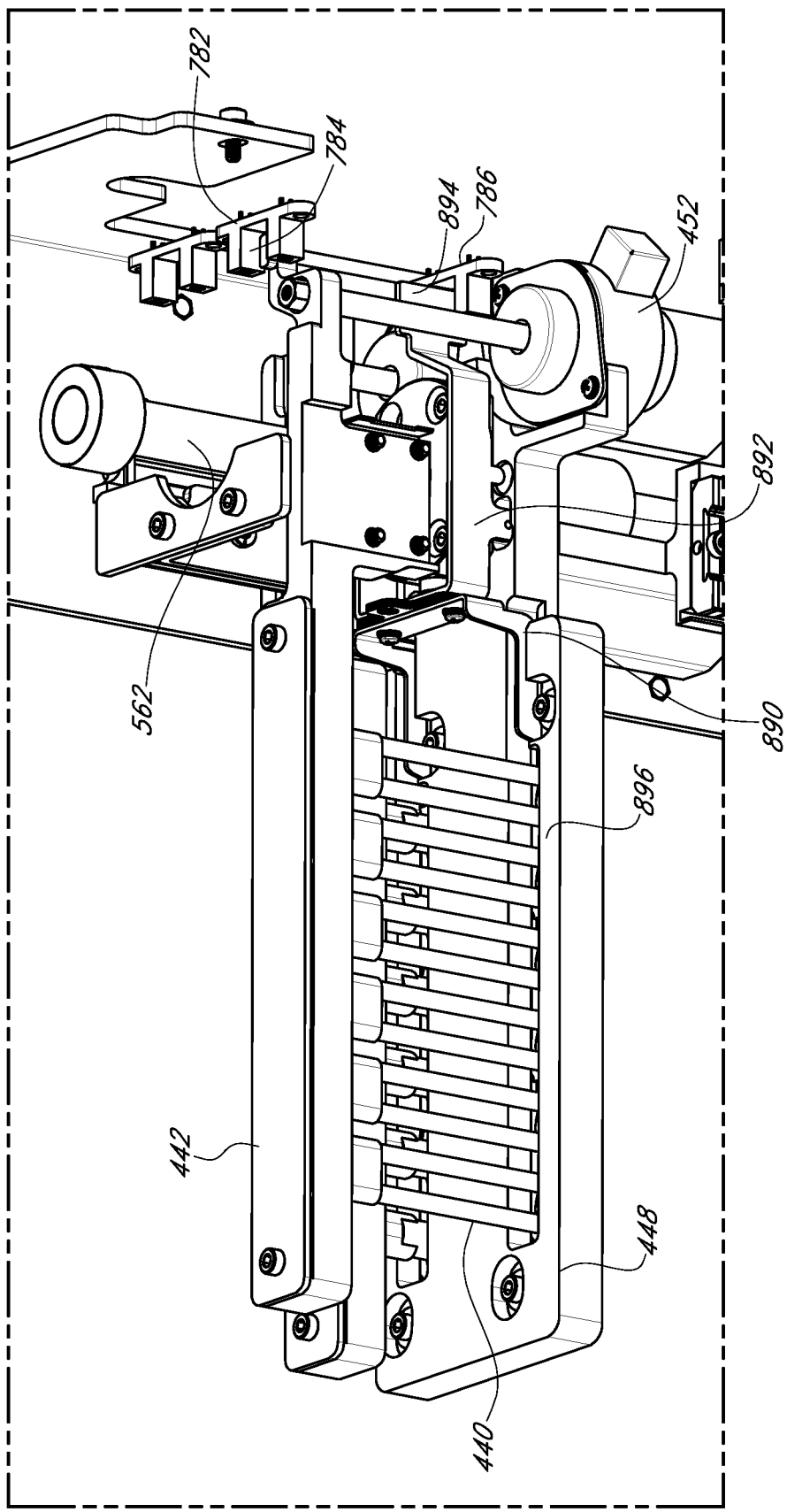
Figure 9:
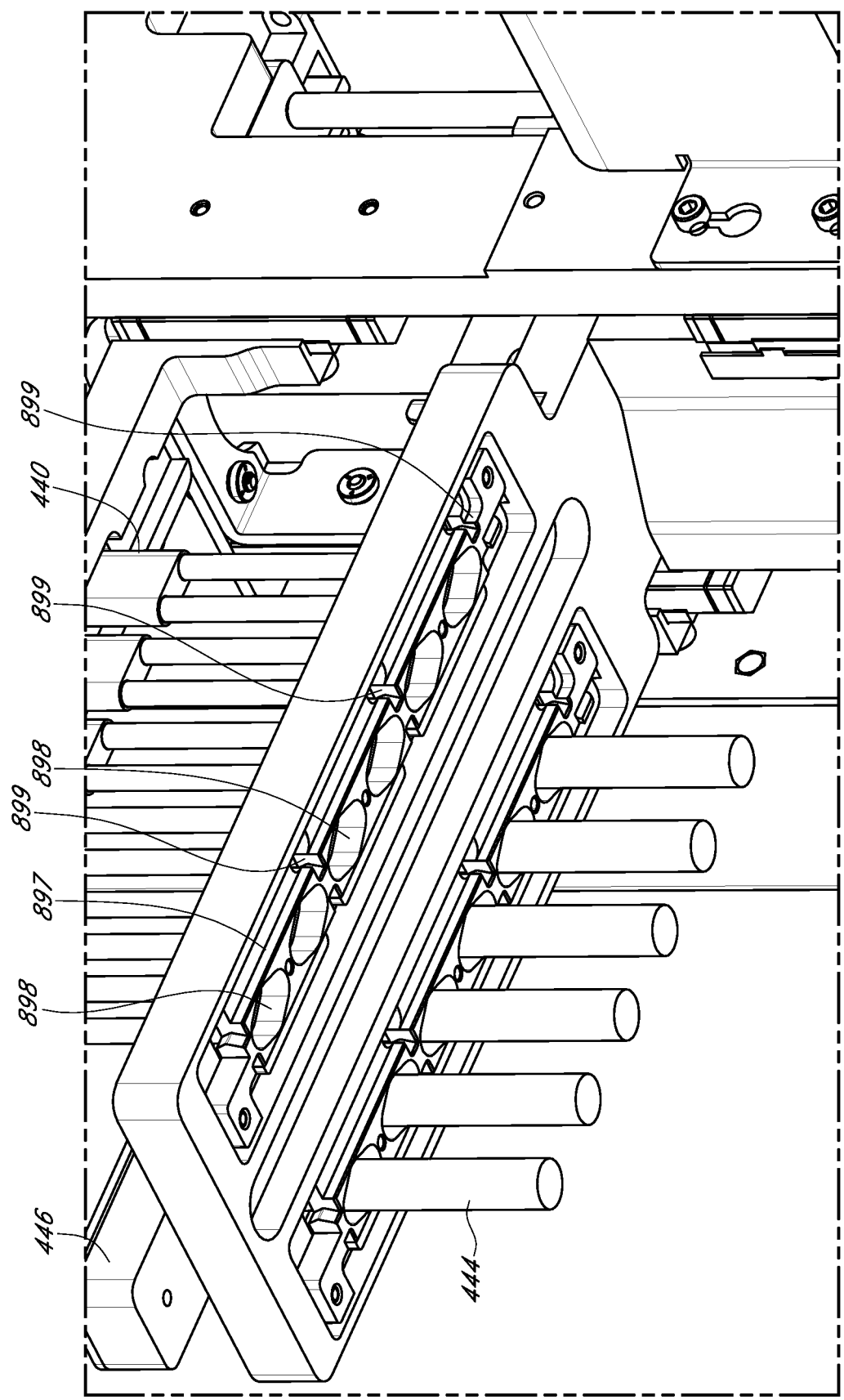

When a selected comb is to be used, the comb is attached to a protective cover. See, for example, FIG. 20 or FIG. 21. The desired comb is lowered relative to the platform 448 into an opening 896, as illustrated in FIG. 8. The platform 448 can include a guide 897 that includes openings 898 to receive rods of the comb, as illustrated at FIG. 9. The guide 897 can further include recesses 899 to engage clips associated with the protective covers. Returning to FIG. 8, the sled 450 and platform 448 can further include a mechanism to detect when the platform is engaging the support securing the protective covers. For example, an arm 890 attached to a lever 892 can rotate in response to engaging the cover support, moving an extension 894 into proximity with a sensor 786. As such, the system can ensure coupling with the protective covers for the comb rods.

Figure 10:
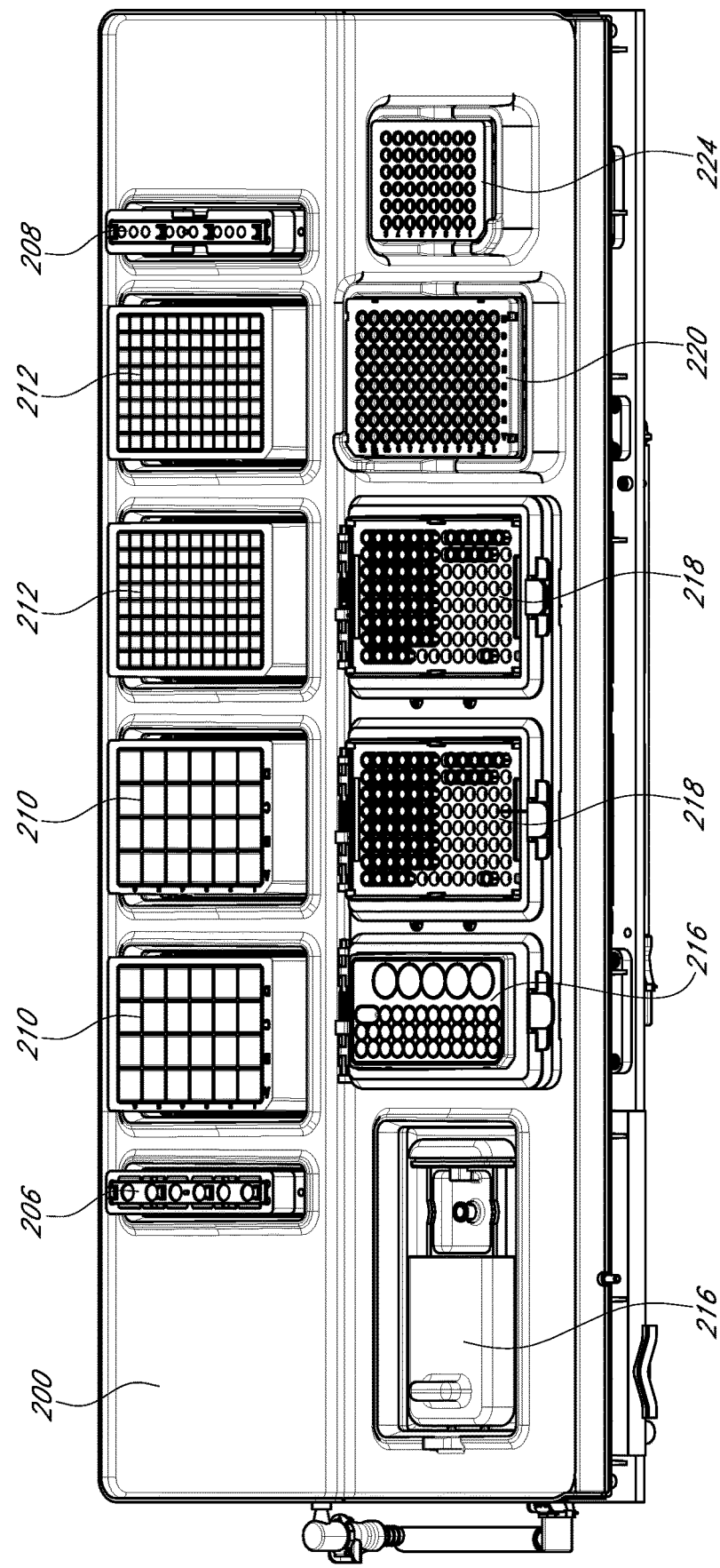
FIG. 10 and FIG. 11 include illustrations of an example deck of the purification system.

As illustrated in FIG. 10, the platform 200 includes cover supports 206 and 208 to hold the protective covers for the magnetic combs. In addition, the system can security different types of plates 210 or 212, including a different number of wells. For example, the plate 210 can include an array of 24 wells, while the plate 212 can include 96 wells.

The deck 200 can further secure a quantitative fluorometer 214 and associated reagent plate 216 with wells for mixing reagents and extracted samples. Portions of the extracted nucleic acids can be stored in a transfer plate 220 and remaining portions of the extracted samples can be stored in an archive plate 222.

Figure 11:
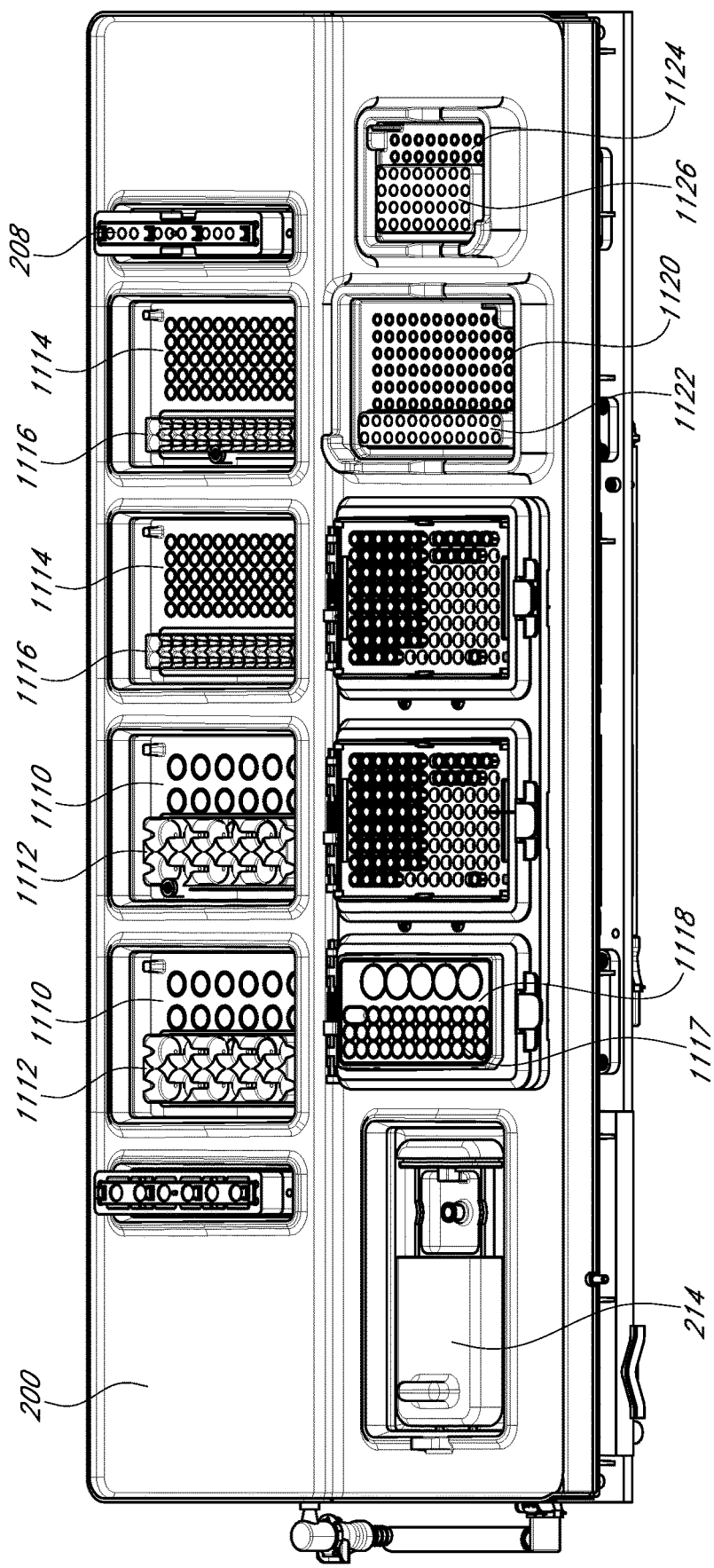

As illustrated in FIG. 11, the receptacles for the various types of plates can include blocks for heating or cooling at least a portion of the wells of the plates. For example, receptacle 1110 to receive a plate 210 can include a temperature control block 1112 for heating or cooling rows of wells of the plate 212. In the illustrated example, the temperature control block 1112 can control the temperature at two rows of wells. Similarly, receptacles 1114 to receive second type of plate 212 can include temperature control blocks 1116 to control the temperature of a number of rows, such as two rows, of the wells of the plate 212. Receptacle 1117 to receive the reagent tray 216 can include one or more temperature control blocks 1118 to control the temperature of some or all of the wells of the reagent tray 216. Similarly, a receptacle 1120 can include temperature control block 1122 to control the temperature of one or more rows of the transfer plate, and a receptacle 1124 can include a temperature control block 1126 to control the temperature of rows of an archive plate 222.

Figure 12:
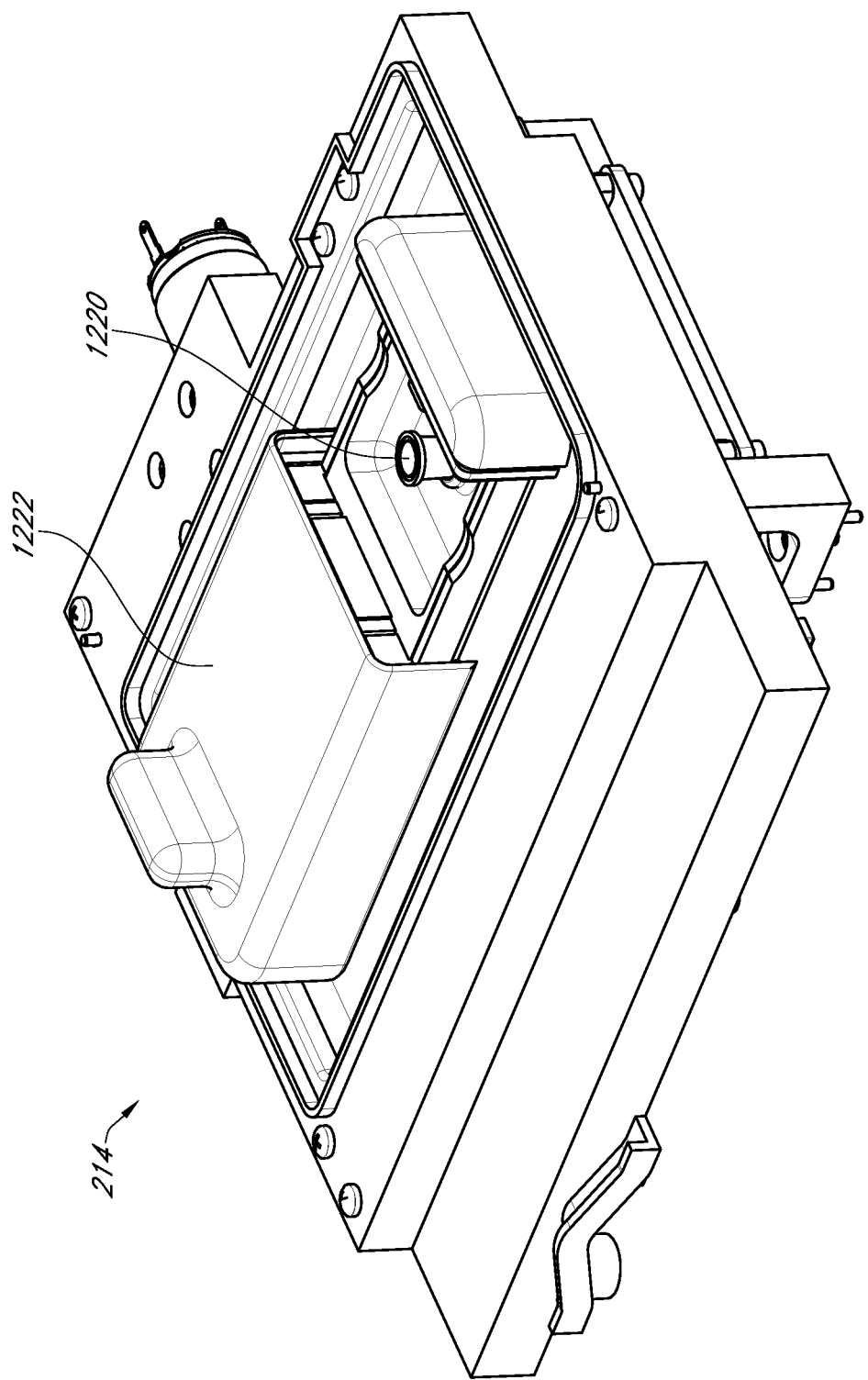
FIG. 12 includes an illustration of an example fluorometer for use with the purification system.

As illustrated in FIG. 12, the system includes a fluorometer 214. In particular, the fluorometer 214 can assist with quantifying a concentration of extracted nucleic acid in a given solution derived from a particular sample. In an example, a proportion of an extracted sample mixed with quantification reagents is inserted into the sample port 1220. An automated lid 1222 may close while the fluorometer 214 takes a measurement.

Figure 13:
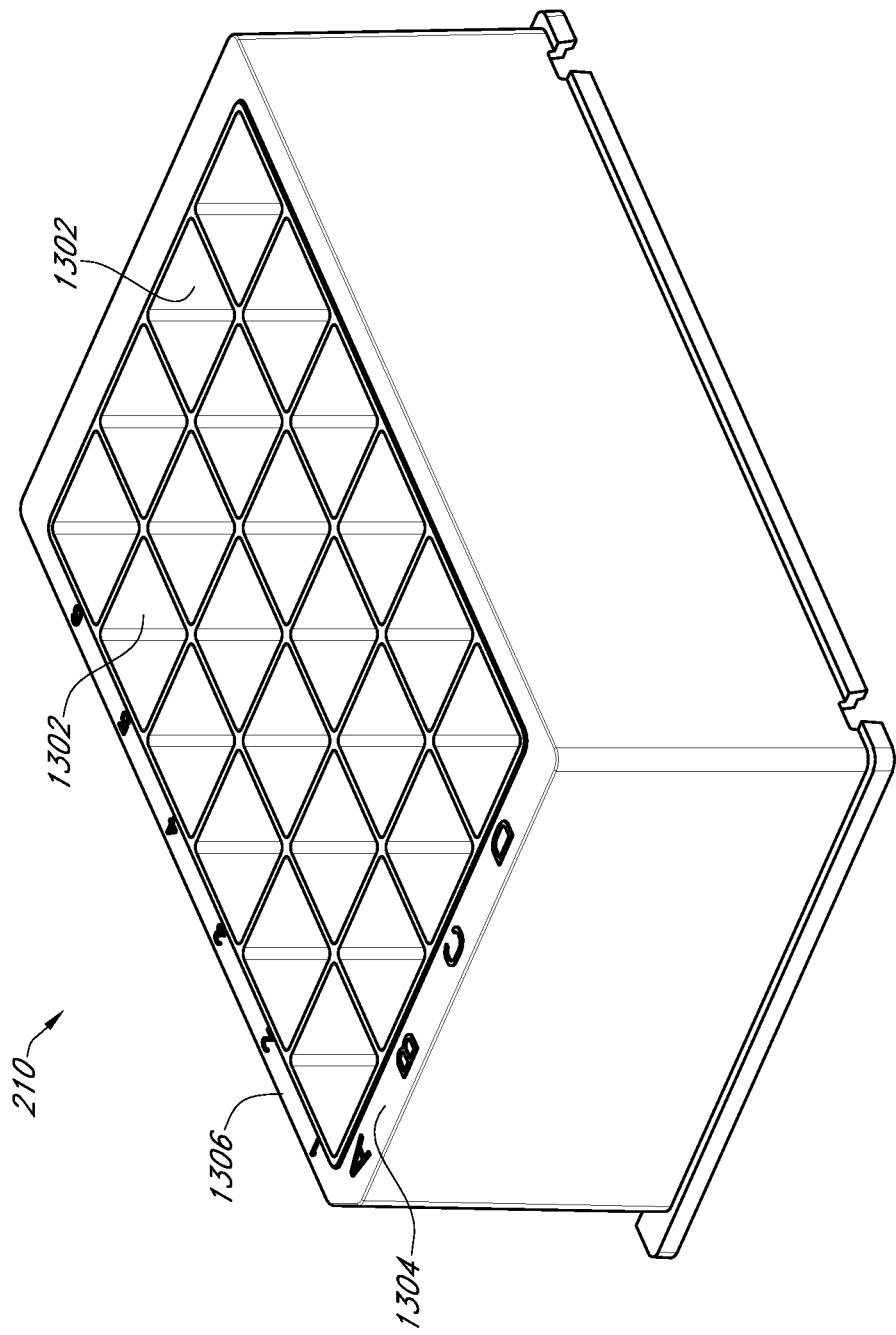
FIG. 13, FIG. 14, FIG. 15, FIG. 16, and FIG. 17 include illustrations of example consumables for use with the purification instrument.
Figure 14:
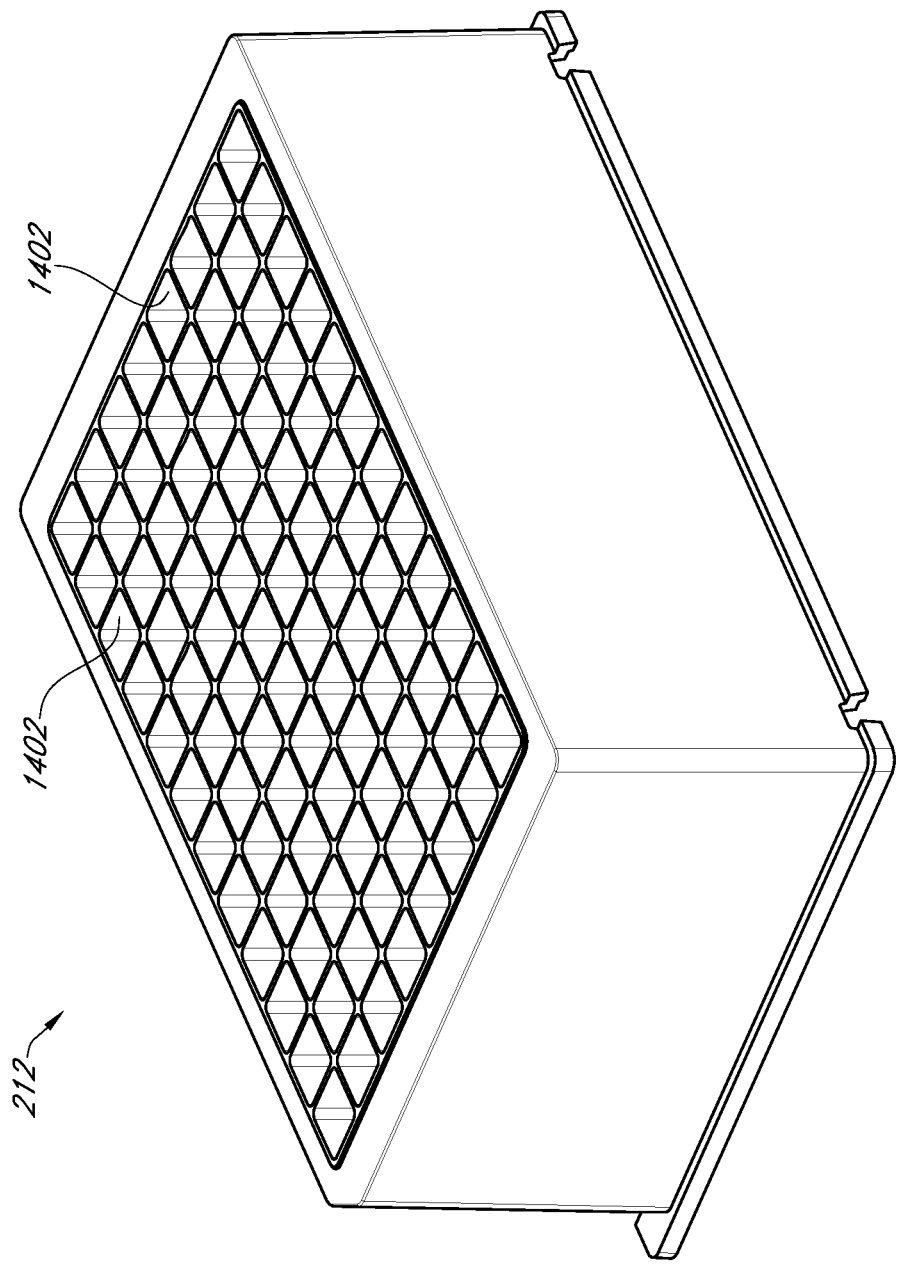

The system can utilize multiple types of plates to perform the extraction process. For example, as illustrated in FIG. 13, a welled plate 210 includes a plurality of wells 1302. For example, the welled plates 210 can include four rows of six wells. In addition, the welled plate 210 can include indicia 1304, indicating a row number, and indicia 1306, indicating a column number. In another example, illustrated in FIG. 14, a multi-well plate 212 can include an array of wells 1402. For example, the multi-well plate 212 can include an array of 96 wells 1402, for example, eight rows of twelve wells.

Figure 15:
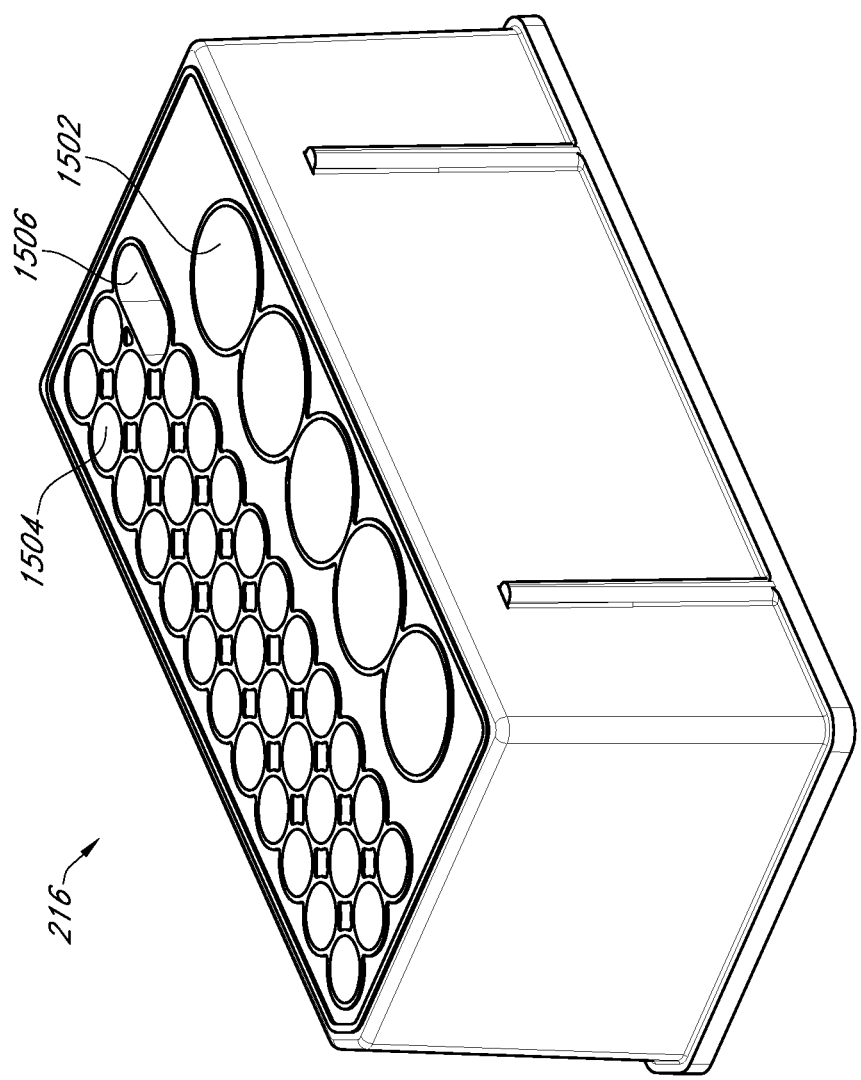

The reagent container 216 illustrated in FIG. 15 can include different types of wells. For example, the plate 216 can include larger wells 1502 for storing reagent solutions and smaller wells 1504 for mixing reagent solutions with extracted samples. In addition, the system can include a well 1506 having a size approximately double that of the smaller wells 1504.

Figure 16:
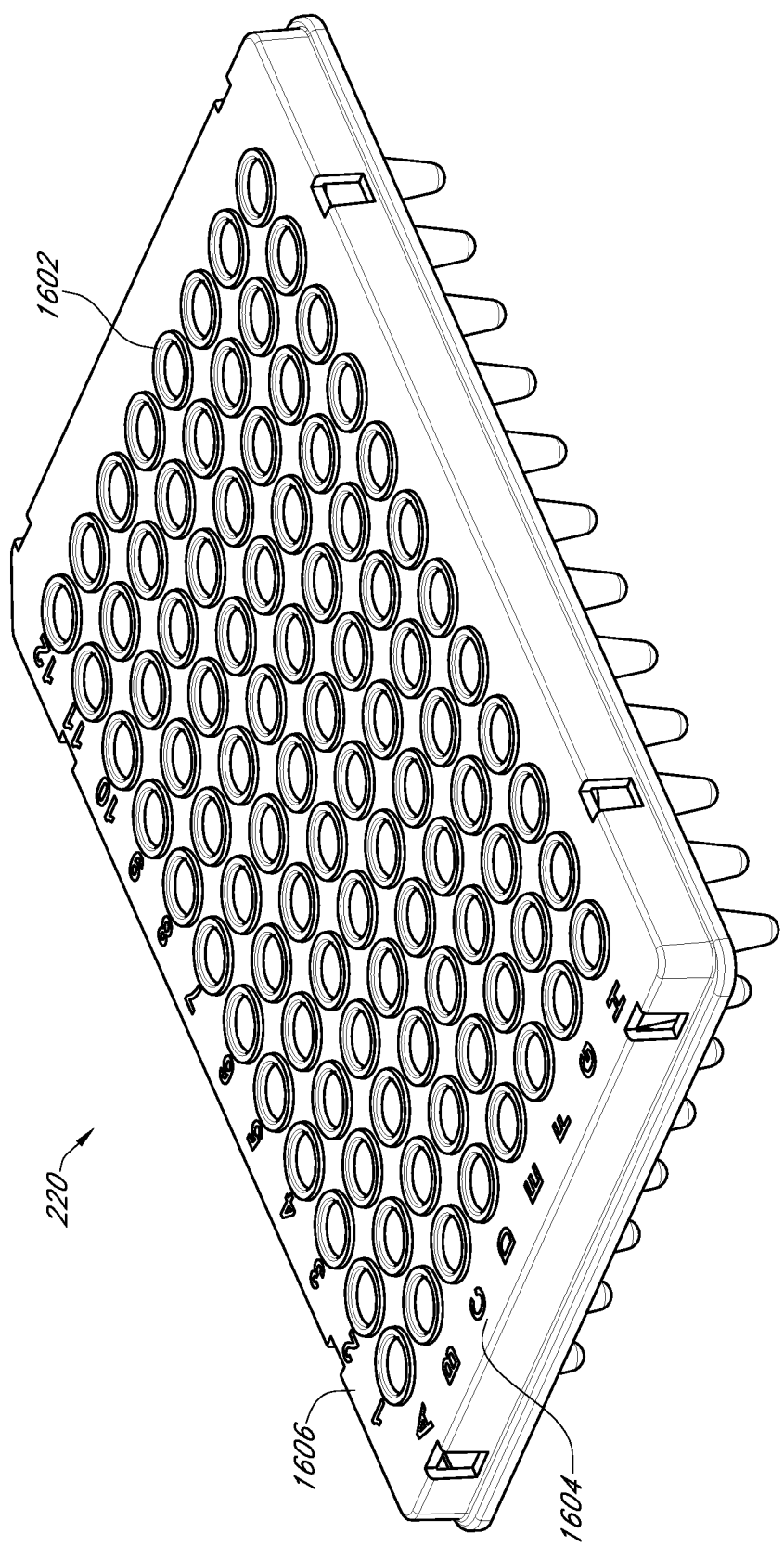
Figure 17:
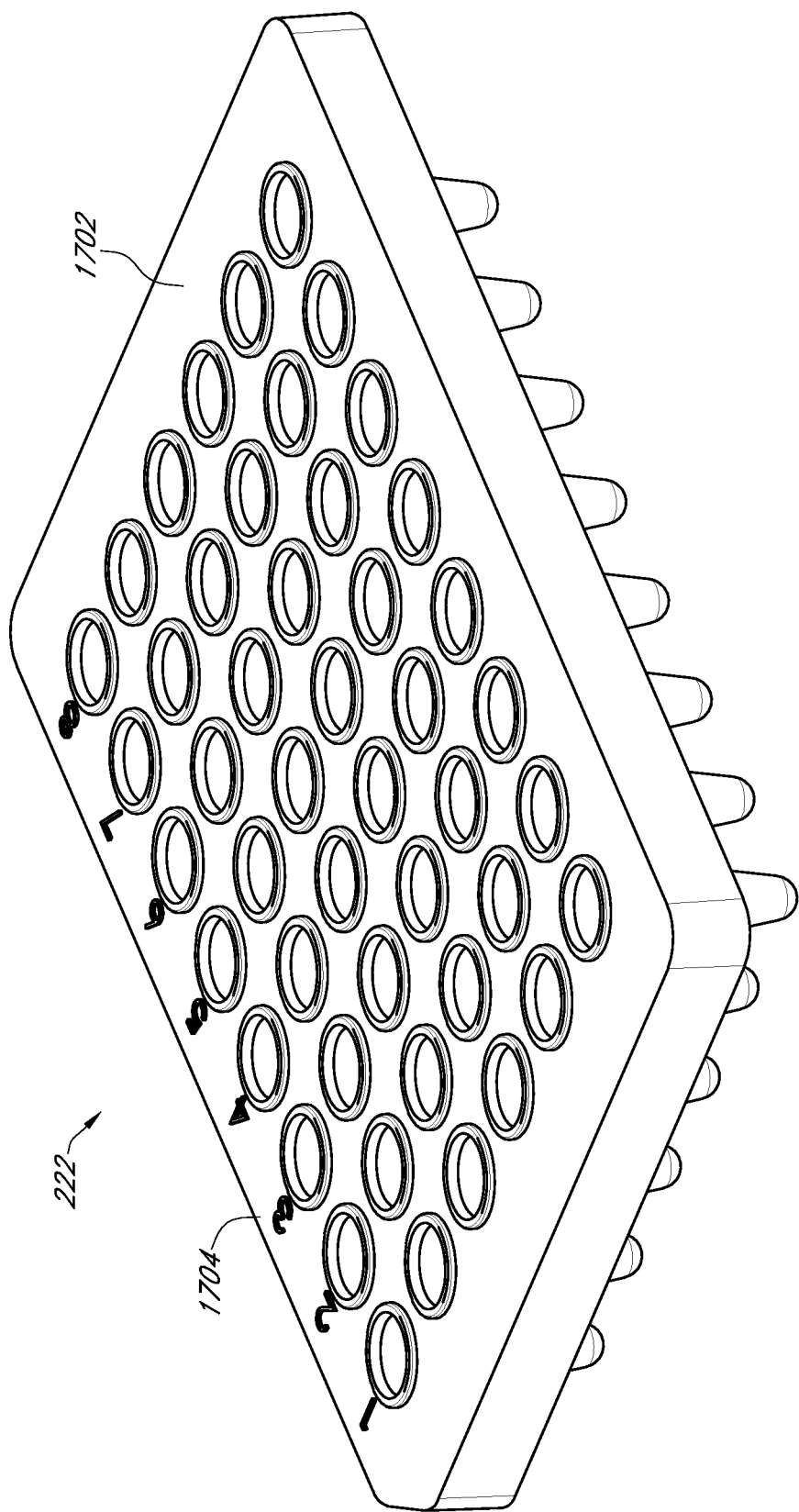

The system can also include a transfer tray of wells for storing extracted samples and a tray of wells for storing extracted samples for archiving. For example, as illustrated in FIG. 16, a transfer tray 220 for storing extracted samples for use by a sequencer can include an array of wells 1602. In addition, the tray 220 can include indicia 1604 of the rows and indicia 1606 of the columns. As illustrated in FIG. 17, and archive tray 222 can include an array of wells 1702 for storing extracted solutions for archiving. The tray 222 can include indicia 1704 indicative of columns and optionally rows. Generally, the archive tray of archive samples is frozen for later use.

Figure 18:
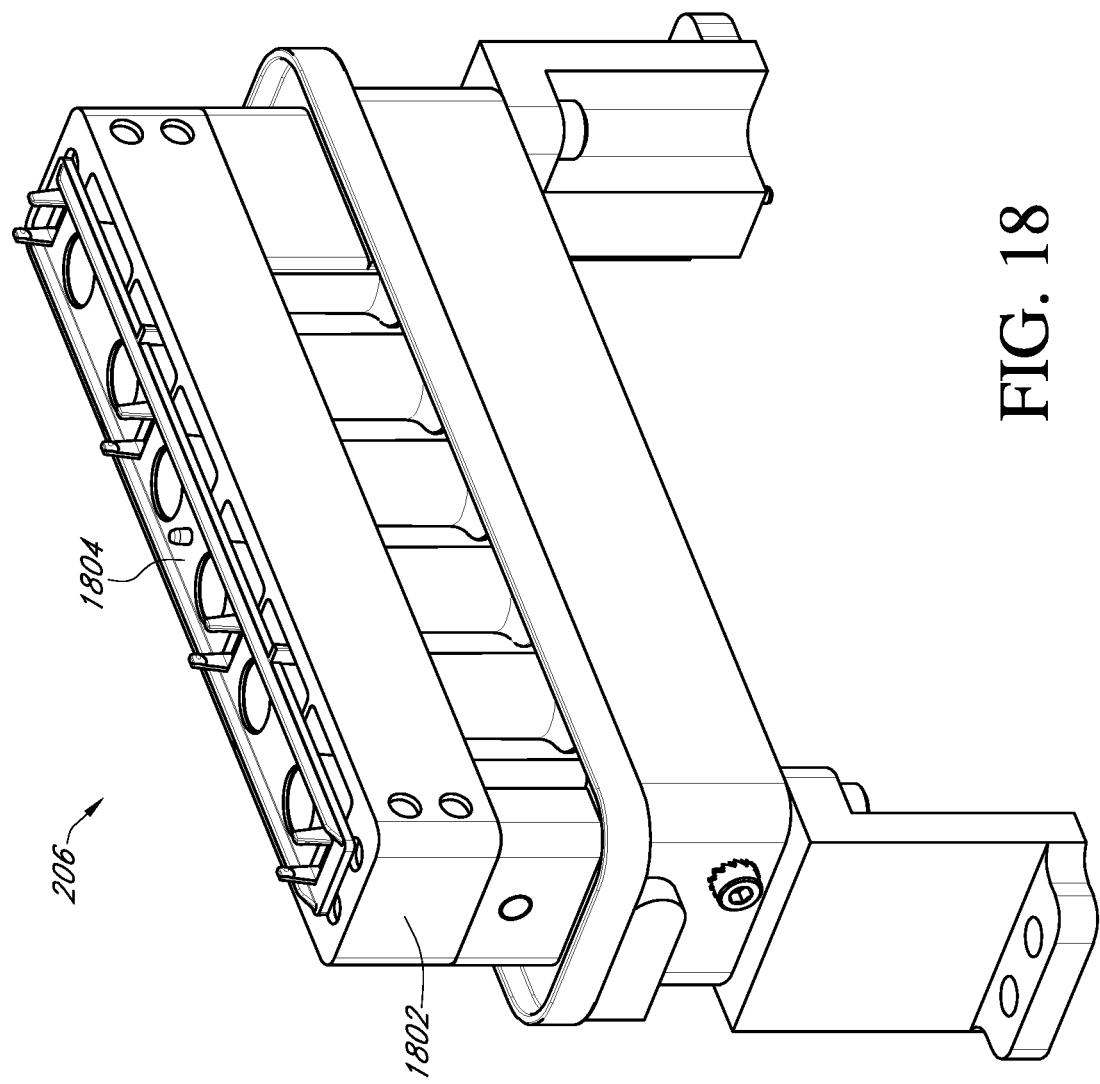
FIG. 18 and FIG. 19 include illustrations of example magnetic comb supports.
Figure 19:
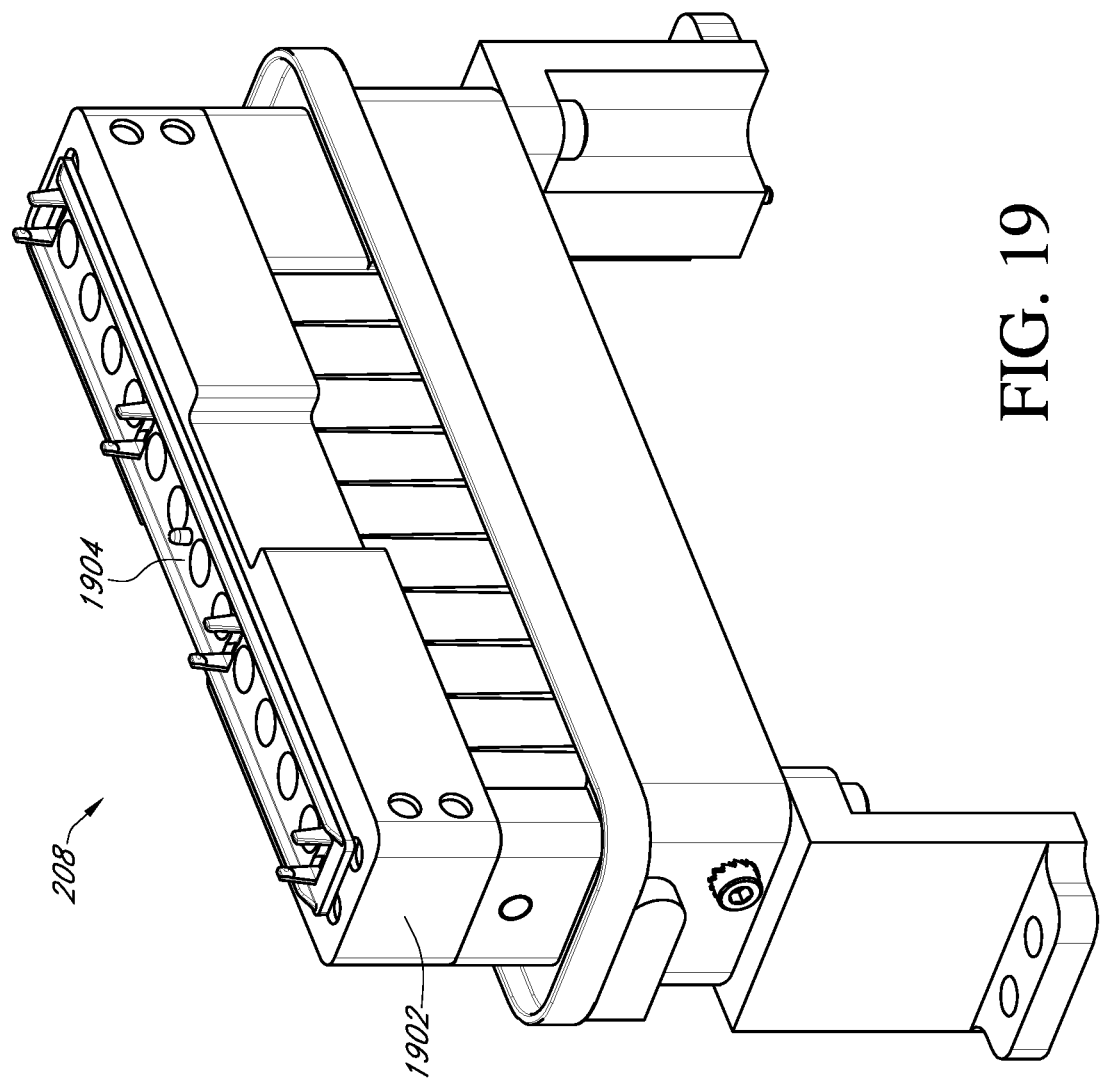

The system can include cover supports to hold the covers for the magnetic combs. For example, as illustrated in FIG. 18, a cover support 206 can include support 1802 to hold the cover 1804 sized for the comb with fewer rods. As illustrated in FIG. 19, a cover support 208 can include the support 1902 to hold a protective cover 1904 for the comb with a larger number rods.

Figure 20:
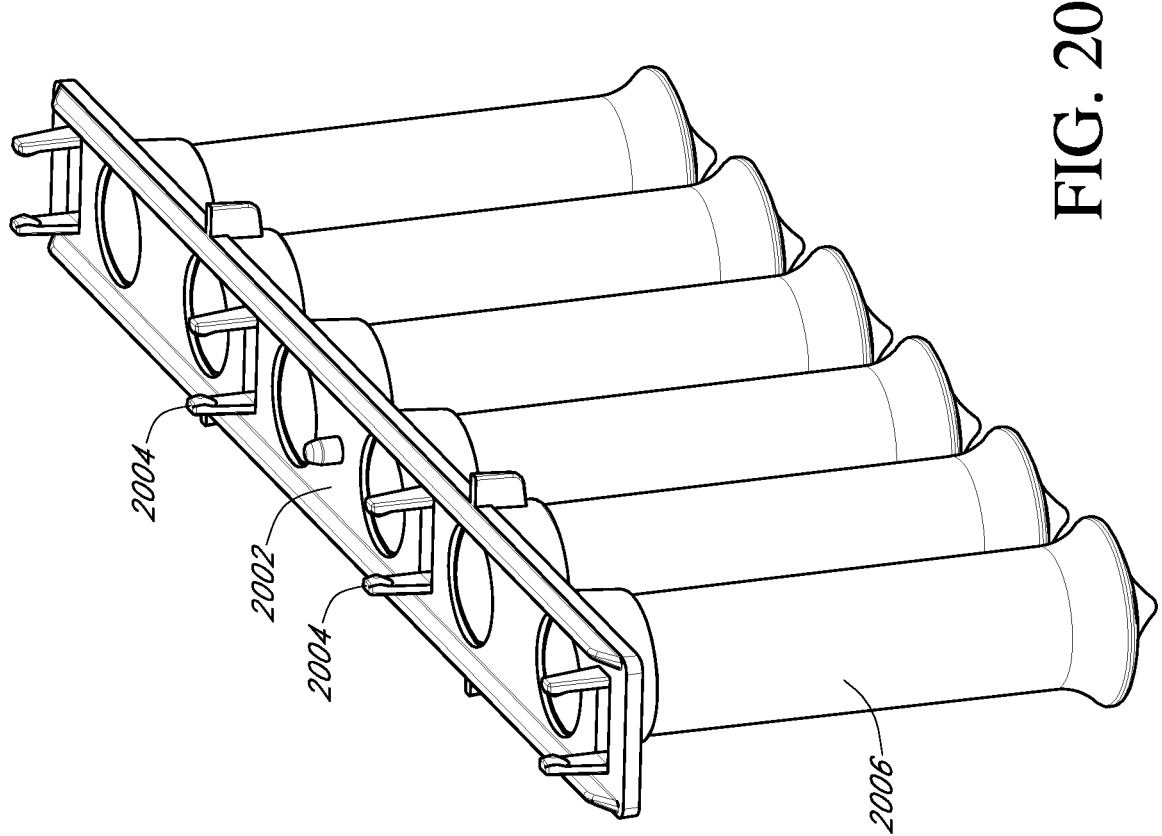
FIG. 20 and FIG. 21 include illustrations of example magnetic comb protectors.
Figure 21:
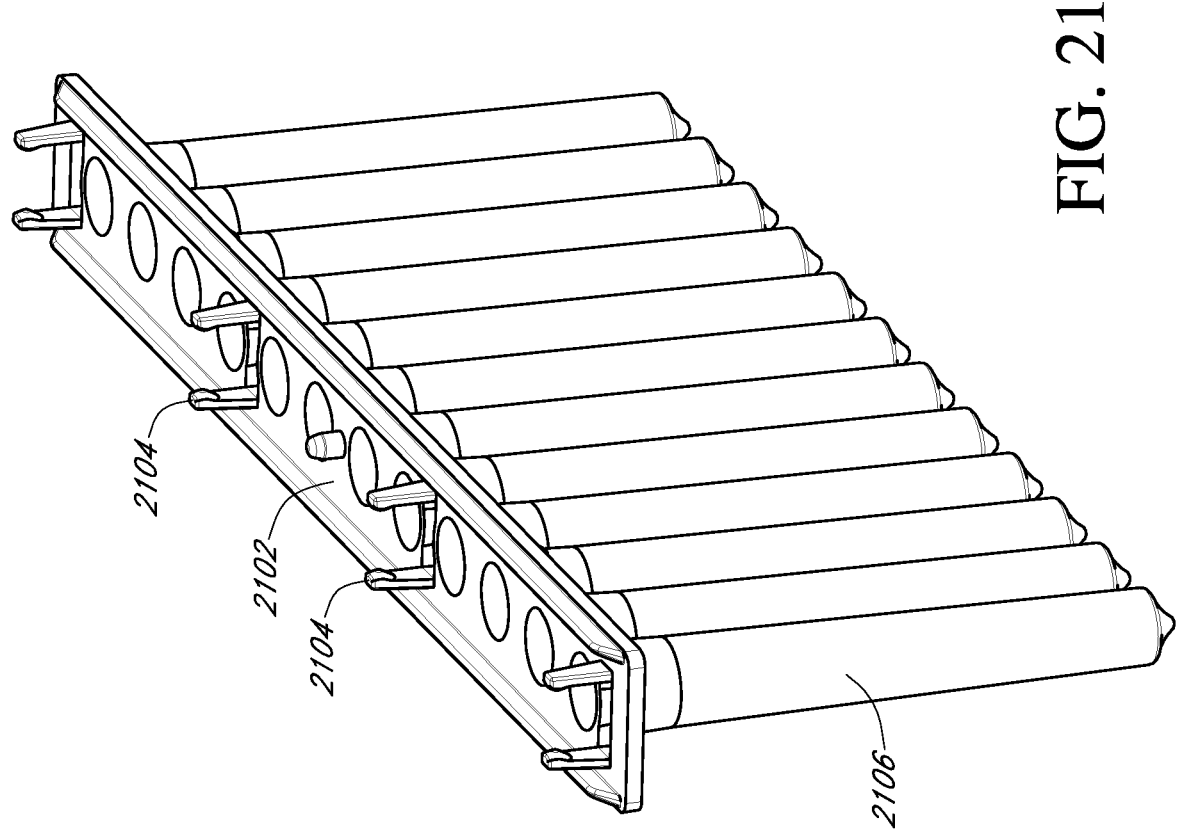

FIG. 20 and FIG. 21 include illustrations of example protective covers. For example, as illustrated in FIG. 20, a protective cover 2002 includes individual covers 2006 for each of the rods. The cover 2002 further includes clips 2004 that attach to the recesses 899 of the guide 897, illustrated in FIG. 9. Similarly, a protective cover 2102 illustrated in FIG. 21 includes a plurality of tubes 2106 to receive the rods of the comb with a larger number of rods. The protective cover 2102 includes clips 2104 to attach to the recesses 899 of the guide 897 illustrated in FIG. 9. In an example, the protective covers are secured to the platform in a fixed position and the magnetic combs can move in and out of the cover by moving up and down relative to the platform. In such a manner, magnetic beads can be captured when the magnet comb is positioned within the cover and can be released when the magnetic comb moves out of the cover. In an alternative example, the cover can be detachably secured to the platform and can be released when the magnet comb is to be moved to release magnetic beads.

The system can utilize various methods to extract nucleic acid based on the sample type and the type of nucleic acid to be extracted. In an example, the sample type can be an FFPE tissue sample, blood, plasma, biological fluids, and other tissues samples.

Figure 22:
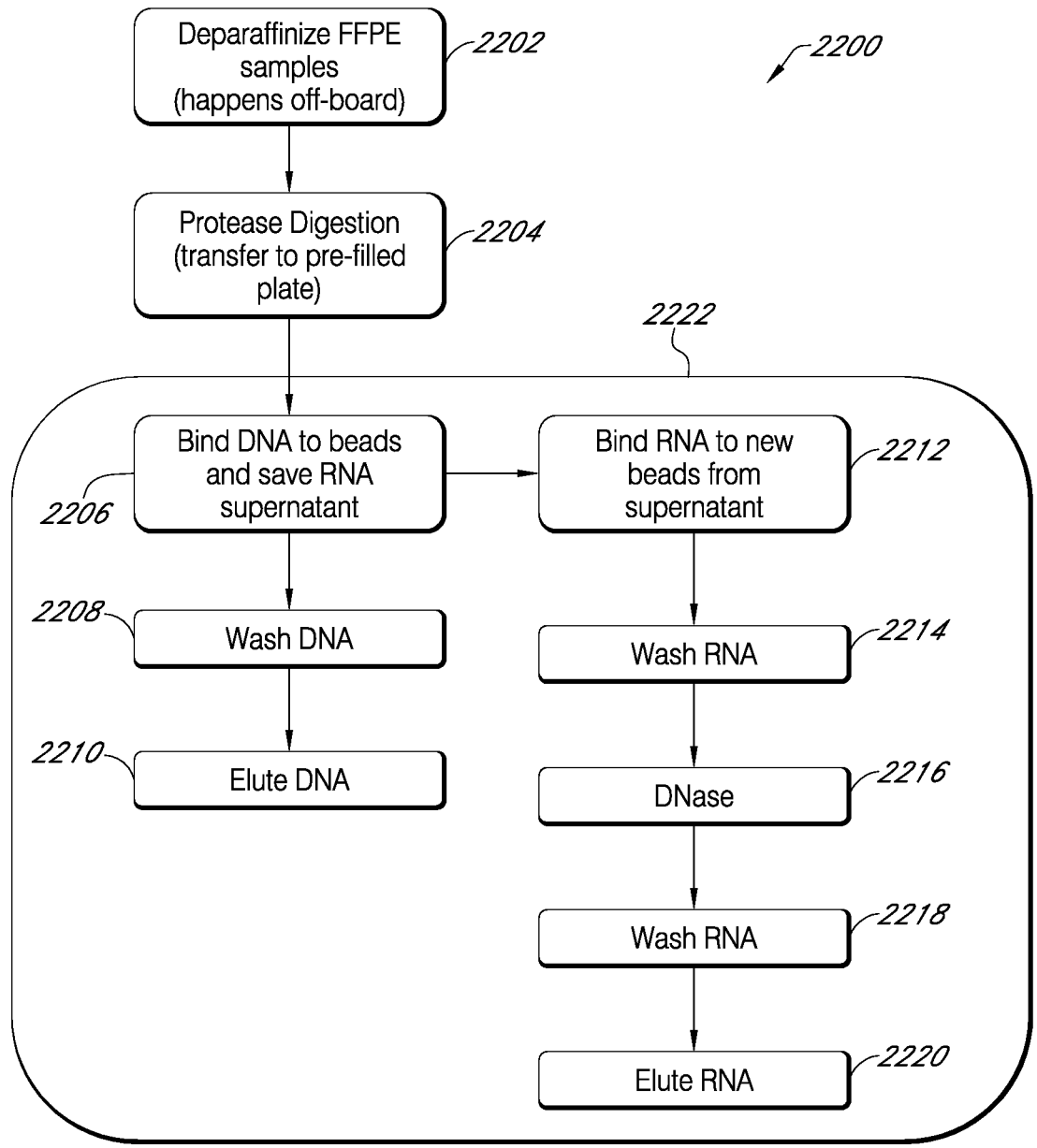
FIG. 22, FIG. 23, FIG. 24, and FIG. 25 include block flow diagrams illustrating example methods for using the purification system.

In an example, FIG. 22 illustrates a method 2200 to extract nucleic acids, including both DNA and RNA, from an FFPE tissue sample. The method 2200 includes deparaffinizing the FFPE sample off instrument, as illustrated at block 2202, and pipetting the sample to a protease digestion solution on a sample tray of the instrument, as illustrated at block 2204.

The instrument can implement automated steps 2222. For example, the instrument can bind DNA to beads and save an RNA supernatant, as illustrated at block 2206. The instrument can wash the bound DNA, as illustrated at block 2208, for example, one or more times using one or more wash solutions, and can elute the DNA, as illustrated at block 2210.

In addition, the system can bind RNA in the supernatant, as illustrated at block 2212. The system can wash the RNA, as illustrated at block 2214. For example, the RNA bound to a bead can be washed one or more times using one or more different wash solutions.

As illustrated at 2216, the RNA solution can be exposed to a DNAs to digest unwanted DNA. The RNA solution can again be washed, as illustrated at block 2218, and eluted, as illustrated at block 2220.

In a particular example, the DNA/RNA purification from an FFPE sample can be conducted using two 96-well plates. Each column of the first 96-well plate can include a row A that includes a binding buffer, row B that includes a beads solution, row C that includes a wash buffer, row D that includes a further wash buffer, row E that includes an additional wash solution, row F that includes a further wash solution, row G that includes an empty well, and row H including an RNA binding buffer. Each column of the second 96-well plate can include a row A with the DNA buffer, an empty row B, row C including an RNA binding buffer, row D that includes an RNA wash buffer, row E that includes a RNA wash buffer, row F that includes a wash solution, row G that includes a wash solution, and row H that includes an RNA beads solution.

In an example, a 200 µL sample can be added to the DNA buffer at the first 96-well plate row A. The DNA elution buffer from a quant consumables reagent tray can be moved to the first 96-well plate at row E. A comb can be used to mix beads at the first 96-well plate row B. The tip, can further be used to bind DNA using the collected beads at 96 well plate row A.

The collected beads can then be moved through wash solutions at row C, D, E, and F. In an example, the collected beads, including the bound DNA can be moved from each of the rows to a subsequent row using a magnetic comb.

After the wash at the first 96 well plate row F, the comb can be allowed to dry outside of the well for a period between 30 seconds and 180 seconds. The tip comb including the collected beads can then be mixed in DNA elution buffer in the first 96-well plate of row G. In an example, the elution buffer is drawn from the reagent tray 216. The comb can be washed for RNA extraction at the first 96-well plate row F.

The comb can be dried outside of the wells for a period between 15 seconds and 60 seconds. The column is dropped into the second plate at row H into the RNA bead solution. Eluted DNA from row G of the first 96-well plate is transferred to the transfer plate. For example, 50 µL is transferred to the transfer plate.

RNA binding buffer is transferred from the first 96 well plate row H to the second 96-well plate at row A. For example, 580 µL of the RNA binding buffer is transferred from the first 96-well plate row H to the second 96 well plate row A. Beads are collected from the second 96-well plate row H and mixed with solution in the first 96-well plate row A. The comb is washed at the 96-well plate row D of the second 96-well plate, and the temperature is controlled at 40° C.

The comb is washed at the second 96-well plate at row F. The beads are dried outside of the well or period of between 36 or 30 seconds to 120 seconds.

The comb is applied to the DNase treatment at the second 96-well plate row A. Thermal control is then disabled. The comb is dries outside of the well and then the cover is dropped at the second 96-well plate row H.

An amount of 450 µL of the binding buffer is transferred to the second 96 well plate row C and 50 µL of the RNA elution buffer from the quantification consumable is transferred to the 96-well plate at row B.

The comb is picked up from row H and applied through the solutions at the second 96 well plate of row A, the second 96 well plate at row E, the second 96 well plate at row F, and the second 96 well plate at row G.

Beads are dried on the comb outside of the wall and the comb is inserted into the RNA elution solution at the second 96 well plate row B. The comb can then be dropped off at row H and 50 µL of the RNA solution buffer can be transferred to the transfer plate.

Figure 23:
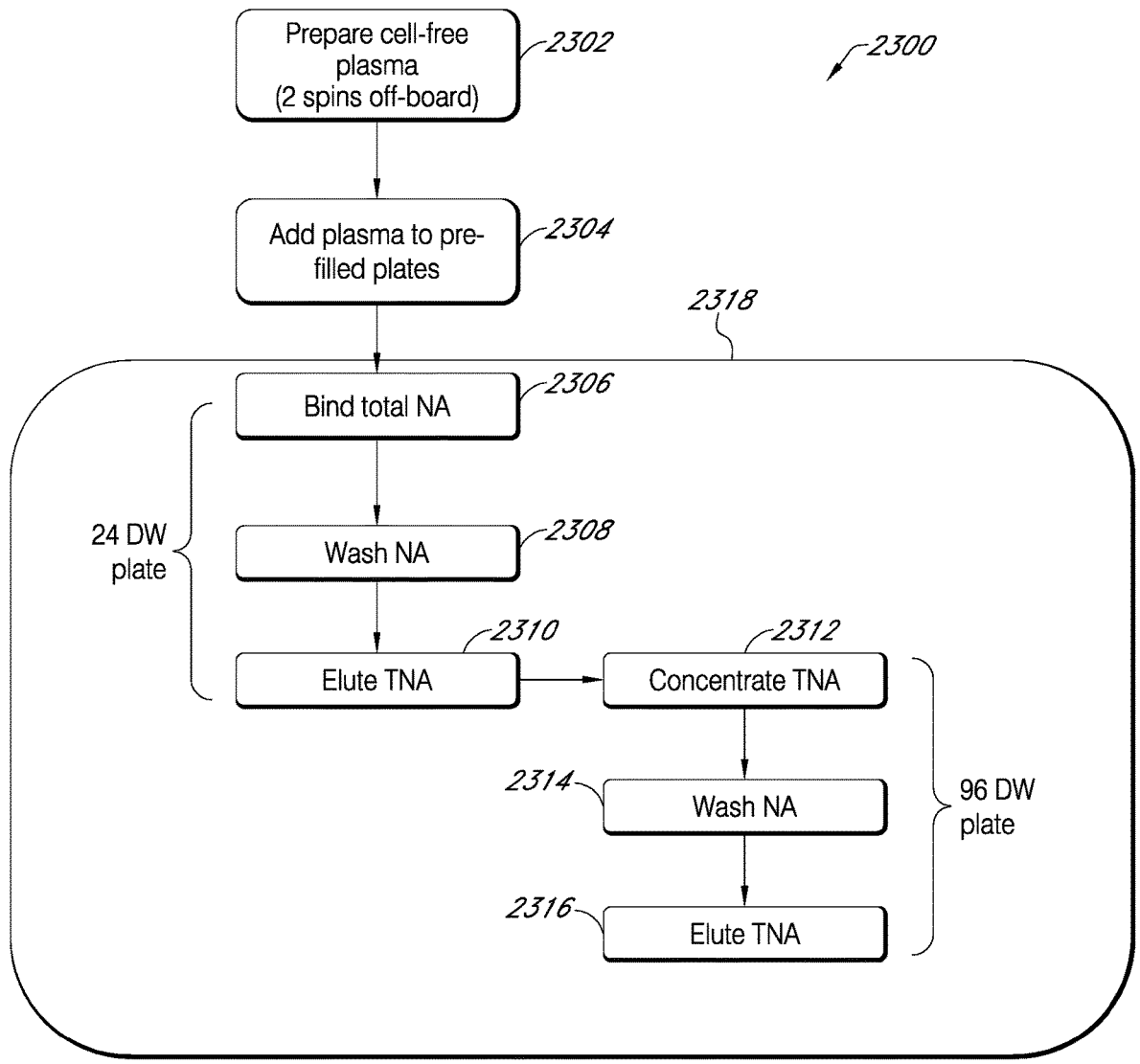

In another example, total nucleic acids can be recovered from plasma, as illustrated in the method 2300 of FIG. 23. For example, the plasma can be prepared, as illustrated at block 2302, and the plasma can be transferred to the prefilled plates as illustrated at block 2304.

The system can then perform the steps automatically, as illustrated at block 2318. For example, total nucleic acid can be bound, as illustrated at block 2306. For example, the total nucleic acids can be bound in a 24-well plate.

The total nucleic acids can be washed, as illustrated at block 2308. For example, the total nucleic acids can be washed by transferring magnetic beads securing the total nucleic acids through a variety of wash solutions. As illustrated at 2310, total nucleic acids can be eluted. For example, total nucleic acids can be inserted into an elution solution.

On a different plate such as a 96-well plate, the system can continue by transferring concentrated nucleic acids, as illustrated at block 2312. The nucleic acids can then again be washed as illustrated at block 2314, and eluted, as illustrated at block 2316.

In a particular example, 2 mL of the sample can be added to the PK digestion on row A of a 24-well plate. Two 24 well plates and a 96-well plate are used. For example, the first 24 well plate can include rows A and B with a PK digestion and rows C and D with the bead solution. The second 24 well plate can include wash solutions at rows A, B, and C and an elution solution at row D. The 96-well plate includes binding buffer at row A, a bead solution at row B, wash solutions at rows C, D, and E, and an elution mix at row F.

In an example, a 2 mL sample is added to a PK digestion solution on rows A and B. The comb is used to collect beads from row C. The comb mixes and collects beads on row D, mixes beads with PK solution on row A and row B, and repeats the collection multiple times. On a second 24 well plate, the comb is used to wash the collected beads on row A of the second plate, washed the beads on B of the second plate, and washed beads on row C of the second plate. The wash can be repeated one or more times with one or more different wash solutions. The comb is dried and mixed with the elution solution on row D. The pipette system is used to transfer elution solution to row A on the 96 well plate.

The elution solution is transferred from the quantification tray to row F of the 96-well plate. A second comb is used to collect beads on row B, mix beads and collect beads on row A, and washed the beads on rows D and E. The beads are then combined with the elution solution on row F. A pipette is used to transfer the eluted samples from row F to the transfer plate 214.

Figure 24:
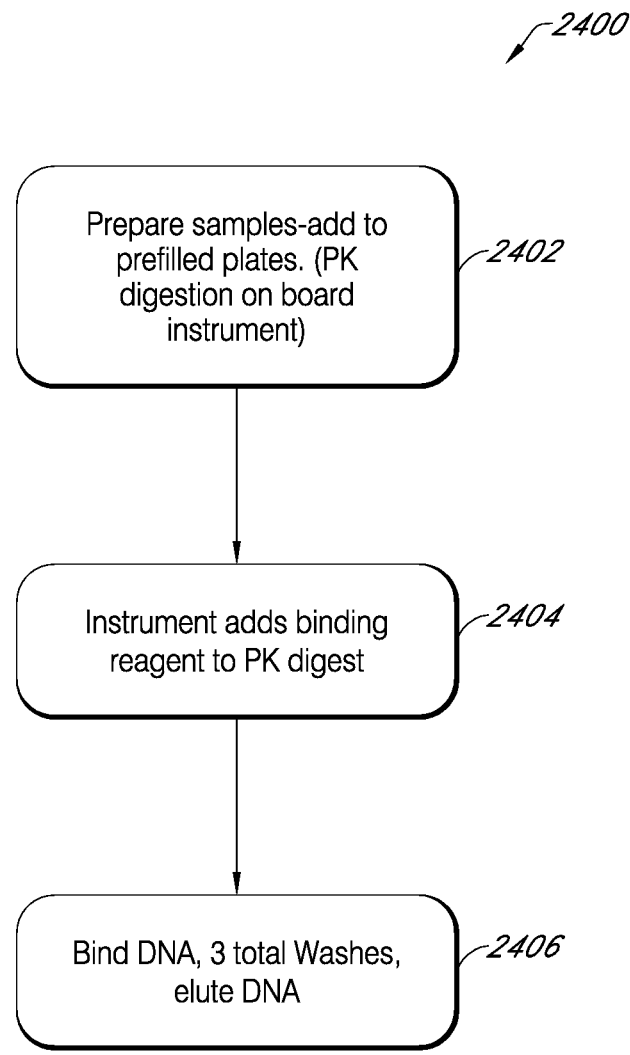

As illustrated in FIG. 24, a method 2400 includes preparing samples and adding the samples to prefilled plates in a row including PK digestion solution, as illustrated at block 2402. As illustrated at block 2404, the instrument adds binding reagent to the PK digestion solution, and as illustrated at block 2406, the system binds DNA, washes the DNA, and dilutes the DNA.

In a particular example, the system applies a thermal control at 65° C., the comb is applied to a PK digestion solution at row A of a 96-well plate. Each column of the plate includes an empty well to which PK digestion solution is applied, an empty well at row B, a well at row C including binding solution, well at row D including a beads solution, wells at rows E, F and G including wash solutions, and an empty well at row H.

The comb mixes the sample at row A in a PK digestion solution. The thermal control is applied to 25° C. The comb then washes the comb at row C. The comb is dried outside of the wells.

A pipette transfers 400 µL of a binding buffer from row C to row A and transfers an elution buffer from the quantification consumable to row B.

The comb is used to collect beads at row D. The comb is applied to facilitate the DNA-binding at row A. The comb is washed at row E. Thermal controls are then set to 63° C. The comb then washes the beads at row F and row G and dries the beads. The beads are then applied to the elution solution at row B. The thermal control is set to 25° C. and a pipette transfers the eluted sample from row B to the archive plate.

Figure 25:
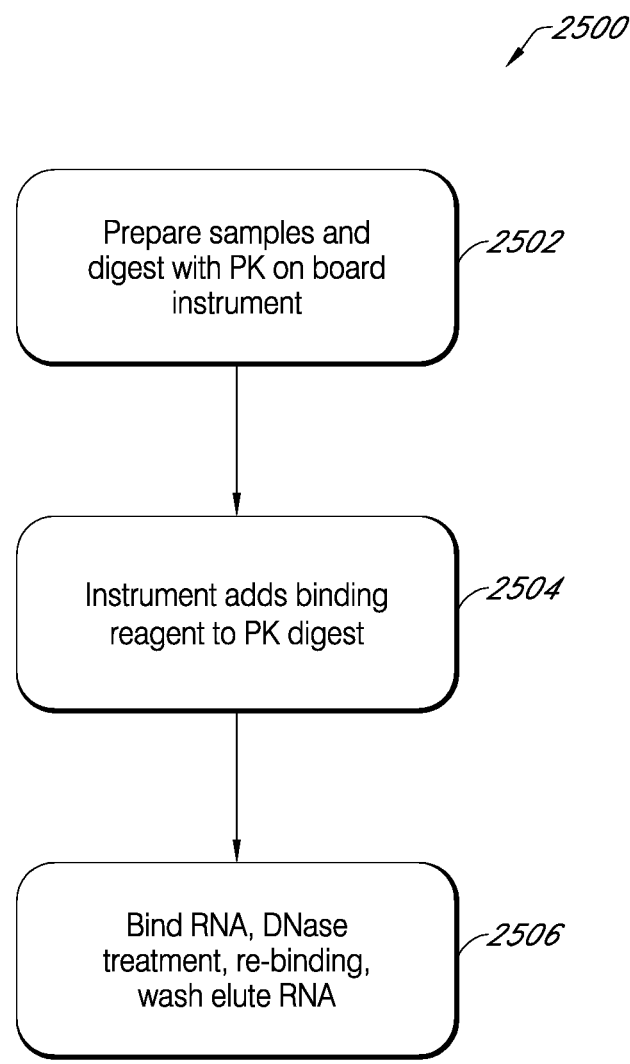

As illustrated in FIG. 25, a method 2500 includes preparing samples and digesting the PK enzyme at a row on the instrument, as illustrated at block 2502. As illustrated, block 2504, a binding reagent is added in the PK digestion solution, as illustrated at block 2506, the system binds the RNA, applies a DNase treatment, re-binds the RNA, and washes to eluted RNA.

In a particular example of extraction from a biofluid, a 96-well plate is used. Each column of the 96-well plate can include a sample well at row A, an RNA elution at row B, a bead solution at row C, a binding solution at row D, wash solutions at rows E and F, a DNase buffer at row G, and an RNA wash solution at row H.

In an example, thermal control is set to 48° C. in preheated for approximately 300 seconds. Thermal controls are then set at 30° C. The comb is used to collect beads from row C, and to transfer beads to the sample at row A. The comb is used to wash at row D A 700 µL microliters of lysis binding buffer is transferred from row D. The comb is then used to mix at row A to collect beads and then wash the beads at rows E and F. The comb is then dried for a period between 60 seconds and 120 seconds.

Already bounded beads are applied to DNase treatment at row G. A 300 microliters of lysis binding buffer is transferred to row G and elution buffer is transferred from quantification consumables to row B and a temperature is set at 68° C.

The comb mixes at row G and collect beads and washes the beads at row H. The comb is then dried for the period of between 60 seconds and 180 seconds. The comb is used to mix beads into the elution solution of row B. Th temperature control is set at 40° C. Mixing is continued at elution row B. The beads are collected, and the temperature control is set to 25° C. Eluted sample is transferred to the archive plate.

In the context of cellular tissue, the method includes transferring 700 µL of the lysis binding buffer to row A. Beads are collected using the comb in row C, are mixed at row A, and washed at row E and F. The comb is dried for a period of between 60 and 180 seconds.

The comb is then used to treat the beads to DNase treatment at row G. 300 µL microliters lysis binding buffer is transferred from to row G, and elution buffer is transferred from the quantification consumable to row B. The temperature control set to 45° C.

The comb is then used to collect beads at DNase treatment of row G, wash the beads at row H, and dry the beads for period of between 60 seconds and 180 seconds. The comb is in used to mix the RNA coated beads in the elution well at row B and collect the beads from which the RNA is disassociated. The thermal control set at 25° C., and the eluted sample is transferred from row B to the archive plate.

While each of the above methods is discussed in relation to actions along a single column, multiple samples or several extractions from the same sample can be performed simultaneously by placing samples in more than one column. As such, depending on the source and assay, the In a first embodiment, a system includes a pipetting system including a 3-axis gantry; a set of magnetic combs; a sled mechanism to select a magnetic comb from the set of magnetic combs; a fluorometer; and a set of receptacles to receive welled plates.

In an example of the first embodiment, the sled mechanism includes a platform, and each magnetic comb of the set of magnetic combs is attached to a separate arm movable vertically relative to the platform. For example, motors are coupled with the sled to move with the sled and to move the arms vertically with respect to the platform. In another example, the system further includes sensors to determine the relative position of the arm with respect to the platform. In a further example, the separate arm is coupled to the sled to move with the sled.

In another example of the first embodiment and the above examples, the system further includes a sensor to detect the position of the sled.

In a further example of the first embodiment and the above examples, the set of magnetic combs includes a first comb having a first number of magnetic robs and a second comb having a second number of magnetic rods. For example, the second number of magnetic rods is twice the first number of magnetic rods.

In an additional example of the first embodiment and the above examples, a receptacle of the set of receptacles is to receive a plate having a first number of wells and another receptacle of the set of receptacles is to receive a plate having a second number of wells different from the first number of wells.

In another example of the first embodiment and the above examples, the system further includes a receptacle to receive a transfer plate.

In a further example of the first embodiment and the above examples, the system further includes a receptacle to receive an archive plate.

In an additional example of the first embodiment and the above examples, the receptacles include temperature control plate to control the temperature of a number of wells of the welled plate.

In a second embodiment, a method for purifying nucleic acids includes applying a sample to a well of a multi-well plate; selecting a magnetic comb from a set of magnetic combs disposed on a gantry system; collecting magnetic beads using the magnetic comb; collecting nucleic acid using the magnetic beads; and eluting the nucleic acid from the beads.

In an example of the second embodiment the method further includes washing the collected nucleic acids prior to eluting the nucleic acid from the beads.

In another example of the second embodiment and the above examples, the method further includes applying a protective cover to the selected magnetic comb automatically using the gantry system.

In a further example of the second embodiment and the above examples, collecting the magnetic beads includes using the gantry system to insert the selected magnetic comb into a set of wells of the multi-well plate that include a magnetic bead suspension.

In an additional example of the second embodiment and the above examples, collecting the nucleic acid includes inserting the magnetic beads collected by the selected magnetic comb into a set of wells of the multi-well plate that includes samples.

In another example of the second embodiment and the above examples, eluting the nucleic acid includes inserting magnetic beads having collected nucleic acid and secured by the magnetic comb into a set of wells of the multi-well plate that includes nucleic acid elution solution.

In a further example of the second embodiment and the above examples, the set of magnetic combs includes a first magnetic comb having a first number of magnetic rods and a second magnetic comb having a second number of magnetic rods different from the first number of magnetic rods.

In an additional example of the second embodiment and the above examples, the method further includes receiving a run type, wherein selecting the magnetic comb is at least in part based on the run type.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A system comprising:
a deck;
a pipetting system including a 3-axis gantry moveable above the deck;
a set of magnetic combs;
a sled mechanism attached to the 3-axis gantry to select a magnetic comb from the set of magnetic combs, the sled mechanism including a plurality of arms, each magnetic comb of the set of magnetic combs is attached to a separate arm of the plurality of arms of the sled, the sled mechanism includes a vertically moveable platform, each magnetic comb of the set of magnetic combs is separately movable vertically relative to the vertically moveable platform, the vertically moveable platform including recesses to selectively engage and release a protective cover associated a select magnetic comb of the set of magnetic combs;

a support attached to the deck to secure the protective cover, the sled mechanism automatically retrieves the protective cover from the support by selectively engaging the protective cover;

a fluorometer attached to the deck and accessible by the pipetting system; and a set of receptacles attached to the deck to receive welled plates which are accessible by the pipetting system.

2. The system of claim 1, wherein each of the separate arms is coupled to the sled mechanism to move with the sled mechanism.

3. The system of claim 1, further including a sensor to detect the position of the sled mechanism.

4. The system of claim 1, wherein a receptacle of the set of receptacles is configured to receive a plate having a first number of wells and another receptacle of the set of receptacles is to receive a plate having a second number of wells different from the first number of wells.

5. The system of claim 1, further comprising a receptacle to receive a transfer plate.

6. The system of claim 1, further comprising a receptacle to receive an archive plate.

7. The system of claim 1, wherein the set of receptacles include a temperature control plate to control the temperature of a number of wells of a welled plate.

8. The system of claim 1, wherein the sled mechanism further includes a mechanism to detect the vertically moveable platform engaging the support securing the protective cover.

9. The system of claim 1, wherein motors are coupled with the sled mechanism to move with the sled and to move the plurality of arms vertically with respect to the vertically moveable platform.

10. The system of claim 9, further including sensors to determine the relative position of the plurality of arms with respect to the vertically moveable platform.

11. The system of claim 1, wherein the set of magnetic combs includes a first comb having a first number of magnetic rods and a second comb having a second number of magnetic rods.

12. The system of claim 11, wherein the second number of magnetic rods is twice the first number of magnetic rods.

* * * * *